United States Patent [19]

Lee

[11] Patent Number: 5,196,523
[45] Date of Patent: Mar. 23, 1993

[54] CONTROL OF GENE EXPRESSION BY GLUCOSE, CALCIUM AND TEMPERATURE

[75] Inventor: Amy S. Lee, San Marino, Calif.

[73] Assignee: The University of Southern California, University Park, Calif.

[21] Appl. No.: 354,988

[22] Filed: May 19, 1989

Related U.S. Application Data

[63] Continuation-in-part of Ser. No. 282,880, Dec. 5, 1988, abandoned, which is a continuation of Ser. No. 690,951, Jan. 1, 1985, abandoned.

[51] Int. Cl.$^5$ .................. C12N 15/11; C12N 15/00
[52] U.S. Cl. .................. 536/23.5; 435/69.1; 435/172.3; 435/320.1; 935/6
[58] Field of Search .............. 435/69.1, 91, 172.1, 435/172.3, 240.1, 240.2, 243, 320.1, 252.3; 935/6, 34, 36, 70, 71; 536/27

[56] References Cited

PUBLICATIONS

Goeddel et al; Nature 290: 20 (1981).
Rosenberg et al: Ann. Rev. Genet. 13:319 (1979).
Kim, Y. and Lee, A., Transcriptional Activation of the Glucose-Regulated Protein Genes and Their Heterologous Fusion Genes by B-Mercaptoethanol, Mol. & Cell. Biol., 7:2974-2976 (1987).
Lee, F. et al., Glucocorticoids regulate expression of dihydrofolate reductase cDNA in mouse mammary tumour virus chimaeric plasmids, Nature 294:228-232 (1981).
Chang, A. et al., Phenotypic expression in *E. coli* of a DNA sequence coding for mouse dihydrofolate reductase, Nature 275:617-624 (1978).
Kramer, R. et al., Regulated expression of a human interferon gene in yeast: Control by phosphate concentration or temperature, Proc. Natl. Acad. Sci. USA 81:367-370 (1984).
Lin, A. et al., Induction of two genes by glucose starvation in hamster fibroblasts, Proc. Natl. Acad. Sci. USA 81:988-992.
Wu, E. et al., Selective Stimulation of the Synthesis of an 80,000-dalton Protein by Calcium Ionophores, J. of Biol. Chem. 256:5309-5312 (1981).
Lee, A. et al., Biochemical Characterization of the 94- and 78-kilodalton Glucose-regulated Proteins in Hamster Fibroblasts, J. of Biol. Chem. 259:4616-4621 (1984).
Pelham, H., A Regulatory Upstream Promoter Element in the Drosophila Hsp 70 Heat-Shock Gene, Cell 30:517-528 (1982).
Karin, M. et al., Activation of a Heterologous Promoter in Response to Dexamethasone and Cadmium by Metallothionein Gene 5'-Flanking DNA Cell 36:371-379 (1984).
Schurr, A. and Yagil, E., Regulation and Characterization of Acid and Alkaline Phosphatase in Yeast, J. of Gen. Micro. 65:291-303 (1971).
Lee, A., The Accumulation of Three Specific Proteins Related to Glucose-regulated Proteins in a Temperature-Sensitive Hamster Mutant Cell Line K-12, J. of Cell. Phys. 106:119-125 (1981).
Lee, A. et al., Transcriptional Regulation of Two Genes Specifically Induced by Glucose Starvation in a Hamster Mutant Fibroblast Cell Line, J. of Biol. Chem., 258:597-603 (1983).

(List continued on next page.)

*Primary Examiner*—James Martinell
*Attorney, Agent, or Firm*—Pretty, Schroeder, Brueggemann & Clark

[57] ABSTRACT

The regulatory sequence for a glucose regulated protein has been isolated. When fused into suitable expression vectors within reading relationship of a desired polypeptide DNA sequence, the resulting hybrid gene can be induced to high levels by glucose starvation, or calcium shock, or by denaturing reagents such as β-mercaptoethanol, in a variety of host systems. Further, the hybrid gene can also be regulated by temperature when it is introduced into temperature-sensitive host systems such as the temperature-sensitive mutant of Chinese hamster cells or other systems having a compatible mutation.

2 Claims, 23 Drawing Sheets

PUBLICATIONS

McCormick, P., et al., Human Fibroblast-Conditioned Medium Contains a 100K Dalton Glucose-Regulated Cell Surface Protein, Cell, 18:173–182 (1979).

Resendez, E. et al., Identification of Highly Conserved Regulatory Domains and Protein-Binding Sites in the Promoters of the Rat and Human Genes Encoding the Stress-Inducible 78-kilodalton Glucose-Regulated Protein, Mo. & Cell. Biol.

Ting, J. and Lee, A., Human Gene Encoding the 78,000-Dalton Glucose-Regulated Protein and Its Pseudogene: Structure, Conservation, and Regulation DNA 7:275–286 (1988).

FIG. 2

```
SmaI
GGGGGGCCC   AACGTGAGGG  GAGGACTTGG  ACGGTTACCG  GTTCTAGGT
CCCCCCGGG   TTGCACTCCC  CTCCTGAACC  TGCCAATGGC  CAAAGATCCA
                              PvuII
GAGAGGCACC  CGAGGACACG  GCAGCTGCTC  AACCAATAGG  AGGGCGGATG
CTCTCCGTGG  GCTCCTGTGC  CGTCGACGAG  TTGGTTATCC  TCCCGCCTAC

CGCCTCTCAT  TGGCGGTCCG  CTAAGAATGA  CCAGTAGCCA  CTGGGGGCG
GCGGAGAGTA  ACCGCCAGGC  GATTCTTACT  GGTCATCGGT  GACCCCCGC

CGTACCAGTG  ACGTGAGTTG  CGGAGGAGGC  CGGCAGCGGC  CAGGGTTGGT
GCATGGTCAC  TGCACTCAAC  GCCTCCTCCG  GCCGTCCGGC  GTCGCAACCA
                                                     StuI
GGCATGAACC  AACCAGGCGG  CTCCAACGAG  ACCAATCGGA  GGCCTCCACG
CCGTACTTGG  TTGGTCGCCG  GAGGTTGCTA  TGGTTAGCCT  CCGGAGGTGC
                                        BsshII
ACGGGGCTGC  GGGGAGGATA  TATAAGCCGA  GTCGGGCGACC  GGGGGCTCG   AATAACCCGG
TGCCCCGACG  CCCCTCCTAT  ATATTCGGCT  CAGCCGCTGG   CCGCCTCG    TTATTGGGCC
                            TATA
```

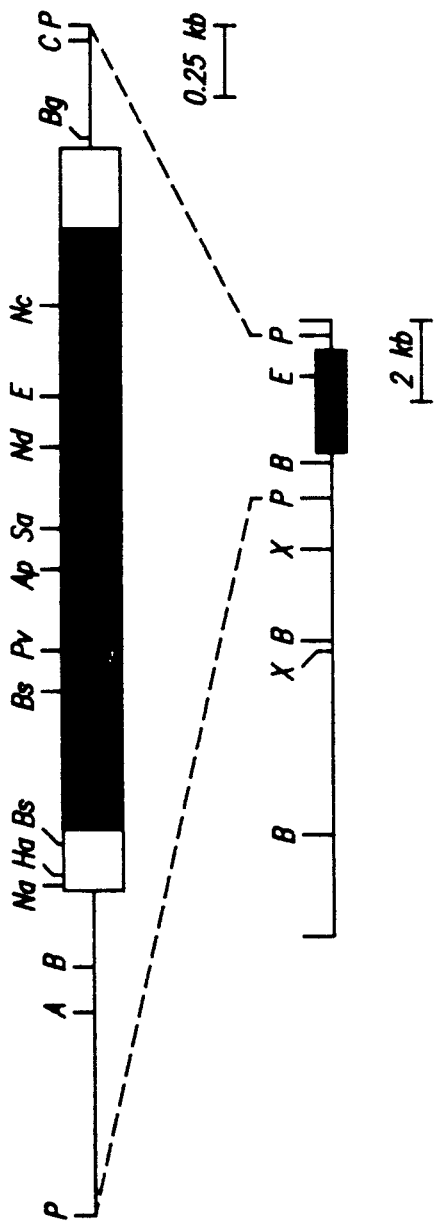

5' ATAGTTCCAACTATATGATTAACCTAGCAAGTATGCTGACCACAGAGTCATACAAGACATCTTTAACTGAAATCCCTCAAATGTTT
GAAAATTAAACAA 5'UTR GAAATTAAACAA
CAACACACTTCTAAATAACATATAGATCTAAAAAAACCATGACACAGAAATTATAAATATTTTGAACCAAATGAAAACTAAACCACACACATCAAAATGTG
CODING 3'UTR poly A
TGAAGTGTAGCTAAATCAATGCTTAGAAATTTATAGCATTAAATGTTTATATTAGAAAATCATAAAATTCTGAAATCAATTCTCTAGTGTTCACCTTAAG 3'

FIG. 17(a)

```
                                                                                                                              120
CCCGGGTCACTCCTGCTGGACTACTCCGACCCCCTAGGCCGGAGTGAAGGCGGGACTTGTGCGGTTACCAGCGGAGTGAAATGCCTCGGGAGTCAGAAGTCGCAGAGGAGAGATAGACAGCTGC

240
TGAACCAATGGGACCAGCGGATGGGCCGGATGTATCTACCATTGGTGAACGTTAGAAACGAATAGCAGCCAATGAATCAGCTGAGAGCGGAGCAGTGACGTTTATTGCGGAGGGGGC

360
CGCTTCGAATCGGGCGGGGCCCAGCTTGGTGCTGGGCCAATGAACGGCCTCCAACGAGCAGGGCCTTCACCAATCGGCGGCCTCCACGACGGGCTGGGGAGGGTATATAAGCCGAGT

480
                                                                                                        M  K  L
AGGCGACGGTGAGGTCGACGCCGGCCAAGAGACAGAGACAGATTGACCTATTGGGGTGTTCGGAGTGTGAGAGGGAAGCGCCGCGGCCTGTATTTCTAGACCTGCCCTTCGCCTGGT

600
TCGTGGCGCCTTGTGACCCGGCCCTGCCGCTGACCCCTGCAAGTCGAAATTGCGCTGCTGCCAAGTCGAAATTGCGCTGCTGGACTGCTGGCACTGACTGGGCACTGGTGGTGGCATCGGCATCGGCACGACTGGGCACGACTGGGGACTGGTGGTGGGCATCGGGCACGACTGACTGGCACGCCACTGGTGGTGGGCATCGGCACGACTGACTTGGGGACCACTACTCCTAAGT

720
 S  L  V  A  A  M  L  L  L  S  A  A  R  A ▼ E  E  E  D  K  K  E  D  V  G  T  V  V  G  I  D  L  G  T  T  Y  S  C <---IN-

840
                                                  INTRON 1--->  V  G  V  F  K  N  G  R  V  E  I  I
TRON 1
GGGGTTGCGGATGAGGGGACGGGGCGTGGGCGTGCCTGGGCTGGGCGTGAGAAGTGCCGGTGCTGTTCAAGAACGGCCGTGGAGATCAT

960
 A  N  D  Q  G  N  R  I  T  P  S  Y  V  A  F  T  P  E  G  E  R  L  I  G  D  A  A  K  N  Q  L  T  S  N  P  E  N  T  V  F
CGCCAACGATCAGGGCAACCGCATCACGCCGTCCTATGTCGCCTTCACTCCTGAAGGGGAACGTCTGATTGGCGATGCCGCCAAGAACCAGCTCACCTCCAACCCGAGAACACGGTCTT

1080
 D  A  K  R  L  I  G  R  T  V  N  D  P  S  V  Q  Q  D  I  K  F  L  P  F  K <---INTRON 2
TGACGCCAAGCGGCTCATCGGCCGCACGGTGAATGACCCGTCTGTGCAGGAGACATCAAGTTCTTGCCGTTCAAGGTTCGACCGGTTTCCTCATCCAGTTAGAGAACGGGTGGGTGGT

1200
GGGAGTATTTAGAGTTATAAGTCTCTGGAAAAGTGTTGAGACAACAGTTGAAGGTTATAGACATGATGATGTTACAAAACTTAAGACAGTTGCT

1320
GTCGTACTGTCTACGATAGTTTAGGAATAAAAGACCTATACTCCCTGAAGTATTTCTAGTCAATTTGAGCCCCAAGGACCAAAATAAACCA

INTRON 2--->  V  V  E  K  K  T  K  P  Y  I  Q  V  D             1440
AATTGTGGGGATGGTAGTGGGTCTTTTAAACTTTGAGATGTCATTGTATCGTGTCTGAAAACAATAATTCTTTAAAATAGGTGGTTGAAAAGAAAACTAAACCATACATTCAAGTTGAT
```

FIG. 17(b)

```
      I  G  G  G  Q  T  K  T  F  A  P  E  E  I  S  A  M  V  L  T  K  M  K  E  T  A  E  A  Y  L  G  K  K <---INTRON 3
      ATTGGAGGTGGGCAAACAAAGAATTTGCTCCTGAAGAAATTTCTGCCATGGTTCTCACTAAAATGAAAGAAACCGCTGAGGCTTATTTGGGAAAGAAGGTAAATATTTCTAGAACAATG    1560

TTAAGTATTTTTGATCATTAGTATTCTCGGTTGGCTGTGTATGTATAGAAGCCTTCGTGTGACGTATTCATGCTTGTCACGGTTTAATTATTGAGT    1680

CCCTTTACTATAAGGCCAAACAAAAATAGACTTTCATGTATTATTTAATGCTTACAGGAACAATAAAATTTATATGTGTATTCATCAATAATTGGCTTAAAAACTAAAGTGA    1800

TGGTTTGACTGTAATTTTTTTTTTTTGAGATGGAGTCTTGCTCTGTTGCCCAGGCTGGACTGCAGTGGCACGATCTCAGCTCACTGCAACCTCTGCCTCCCGGGTTAAGCAGCTCTCCTG    1920

CCTCAGCCTCCAAGTAATGAACGACAGGCACACCACCACAGCTGGCTAATTTTTTTTTTTTTTAATTTCAGTAGAGACAGGGTTCTCCACATTGCCAGGCTGGTCTTGAAATCC    2040

TGCCCTCAGGTGATCCTCCTGCCTAGCCTCCCAAAGTGCTGGATTATAGGCAGAAGCCACCGCTGGCCAGTGTAATTTAAATAAGGGTAAACTATGTGACAATACACTTAATTAT    2160

INTRON 3--->V  T  H  A  V  V  T  V  P  A  Y  F  N  D  A  Q  R  Q  A  T  K  D  A  G  T  I  A  G  L  N  V  M  R  I  I
      CTTTATCCTTTTAGGTTACCCATGCAGTTGTTACTGTACCAGCTATTTTAATGATGCCAAGCAGCCAAGAGCGCTGGAACTATTGCTGGCCTAAATGTTATGAGGATCATCA    2280

INTRON 4--->    T  A  A  I  A  Y  G
      ACGAGCGTAAGTATGAAATTCAGGATACGGCATATTTGCCAAATAGTGAAATGTGAAGTACTGACAAAACTTTCCCTTTTTCAATCTAATAGTACGGCCAGCTGCTATTGCTTATGG    2400

N  E  P <---INTRON 4    L  D  K  R  E  G  E  K  N  I  L  V  F  D  L  G  G  G  T  F  D  V  S  L  L  T  I  D  N  G  V  F  E  V  V  A  T  N  G  D
      CCTGGATAAGAGAGGGGAGAAGAACATCCTGGTTGTTGACCTGGGTGGCGGAACCTTCGATGTCTCTCTCACCATTGACAATGGTGTCTTCGAAGTTGTGGCCACTAATGGAGA    2520

T  H  L  G  E  D  F  D  Q  R  V  M  E  H  F  I  K  L  Y  K  K  K  T  G  K  D  V  R  K  D  N  R  A  V  Q  K  L  R  R
      TACTCATCTGGGTGAAGACTTTGACCAGCGTGTCATGGAACACTTCATCAAACTGTACAAAAAGAAGACAATAGAGCGTGCAGAAACTGCAGAGTCAGGGGCG    2640

E  V  E  K  A  K  A  L  S  S  Q  H  Q  A  R  I  E  I  E  S  F  Y  E  G  E  D  F  S  E  T  L  T  R  A  K  F  E  E  L  N
      CGAGGTAGAAAAGGCCAAGGCCCTGTCTTCTCAGCATCAGGCAAGAATTGAGATTGAGTCCTTCTATGAAGGAGAGGACTTTTCTGAGACCCTGACTCGGGCCAAATTTGAAGAGCTCAA    2760

INTRON 5--->  D
      M <---INTRON 5
      CATGGTATGTTCCTTGTGTTTCTGCTTGCTAATGAGATCTCCTTAGACTCTGAATTCAGGACATTCAGGACATTGCATCTAGATACTTAGATAACAGACATCACAGTAACCATGTCTTTTTCTAGGAT    2880
```

FIG. 17(c)

```
     L F R S T M K P V Q K V L E D S D L K K S D I D E I V L V G G S T R I P K I Q Q
     CTGTTCCGGTCTACTATGAAGCCCGTCCAGAAAGTGTTGGAAGATCTGATTTGAAGAAGTCTGATATTGATGAAGTCTTGTTGGTGGCTGGACTGAACTCGAATTCCAAAGATTCAGCAA 3000

L V K E F F N G K E P S R G I N P D E A V A Y G A A V Q A G V L S G D Q D T    <--IN-
     CTGGTTAAAGAGTTCTTCAATGGCAAGGAACCATCCCGTGGCATAAACCCAGATGAAGCTGTAGCGTATGGTGCTGCTGTCCAGGCTGGTGTGCTCTCTGGTGATCAAGATACAGGTAGG 3120

TRON 6
     TCATCATCGCAGCATCTTTCTTAGTGATTCAGTAGCTTGATGGAAGAGCTCGGTACCCCTATTGCTTTAGAAAATACCAGAATATGAGCAACAAGGTCACACAGCTAGTAAAGGGTATAA 3240

GTGAAGACAAGACTGGGTAGTCTCCAAGATCATTAGCAACTGTTTAATTCACTGCCTTAAAAATGTGTGTGTTAGAACCTAACCAAATGTTAGAGAGATAAACTTTACATAGCTCATAG 3360

INTRON 6-->G D L V L L H V C P L T L G I E T V G G V M T K L I P
     GGAGAACTTGAATTAAAAGTTAAATAACTTATCCTTACAGGTGACCTGACTGGTACTGCTTCATGTATGTCCCCCTTACACTGGTATTGAAACTGTAGGAGGTGTCATGACCAAACTGATTCCA 3480

S N T V V P T K N S Q I F S T A S D N Q P T V T I K V Y E   <--INTRON 7
     AGTAATACAGTGGTGCCTACCAAGAACTCTCAGATCTTTTCTACAGCTTCTGATAATCAACCAACTGTTACAATCAAGGTCTATGAAGGTAATTACCTTAAGTTTGGTTAATATCATGGC 3600

TTTTTTTTTGAGATGAAGTCTTGCTCTGTTGCCCAGGCTGACTGCAGTGGCACGATCTCGGCTCACTGCAAATTCTGTCTCCCAGGGTTCAAGTGATTCTCCTGCCTCAGCCTCCAGAGT 3720

AGCTGGGATTACAGCCTGACCACCACCACCTGGCTAATTTCTGTATTTTTAGTAGAGGATGGGCTTTCACCATGTTTCCCAGGCTGGTCTCGAACTCCTGACCTCAGGTCATCTGCCTGCCT 3840

CCACCGTCCCGAAAGTACTGGGATTATAGCGTGAGCCACCACGCCCAGATCTATCATCATGGCATATTTTAAAAGAACATGACTTAATATGTCCTATTGAAATGCTAGGAACTAAGTA 3960

ACTGTGTTTCAGATGAGGTCTTAATTGAATAATGTGATATTAGATATTTAGCATTCTTTTTTTTTTTTAATGGAGTCTTGCTCTGTCGCCTAGGCTGGGGTGCAGTGGCAT 4080

GACTTGCAACCTCTGCCTCCCGAATAGCTGGGATTACAGGTGCCACCATCACGCCCGGCTAAGTTTGTATTTTTAGTAGAGGGCCAGTTCGCCATGTTGGCCAGGCTGGTCTTGAACC 4200

CCTAACCTCAGTGATCCCACGGTCACCGACCTGGCCTCCCAAAAGTACTGTACCCAGCCAATGATTAGCATTCTCACTAATAATAGCATCTGAGCTGGCCTCCTAGAGTAACAAGAAAAAGG 4320
```

FIG. 17(d)

```
AGTCCACAGTACTTTAAAATAGATAAAATTCAGTTGAGTTAGTAACCTAACCTCATTGTTAGTACTAGTTGCTGCTCCTTGTAGACCAATATGAAATTACTTTTAGCTCGATAAAACCAAA 4440
                                                                                                      INTRON 7--->G  E R P L T K D N
AGTGTCACTTTATGCTTCAGACTGAAATGCGGGGATCTAGATGTGCTAATGCTGTCAGTAACAACTAACAAGTTTTTCTGTATGTAACTTCTAGGTGAAAGACCCTGACAAAAGACAA 4560
   H  L L G T F D L T G I P P A P R G V P Q I E V T F E I D V N G I L R V T A E D K
TCATCTTCTGGGTACATTTGATCTGACTGGAATTCCTCCTGCTCCTCGTGGGTCCCACAGATTGAAGTCACCTTTGAAGATAGATGTGAATGGTATTCTTCGAGTGACAGCTGAAGACAA 4680
   G T G N K N K I T I T N D Q N R L T P E E I E R M V N D A E K F A E E D K K L K
GGGTACAGGGAACAAAAAATAAGATCACAATCACCAATGACCAGAATCGCCTGACACCTGAAGAAATCGAAAGGATGGTTAATGATGCTGAGAAGTTTGCTGAGGAAGACAAAAAGCTGAA 4800
   E R I D T R N E L E S Y A Y S L K N Q I G D K E K L G G K L S S E D K E T M E K
GGAGCGCATTGATACTAGAAATGAGTTGGAAAGCTATGCTTATTCTCTAAAGAATCAGATTGGAGATAAAGAAAAGCTGGGAGGTAAACTTCCTCTGAAGATAAGGAGACCATGGAAAA 4920
   A V E E K I E V L E S H Q D A D I E D F K A K K E L E E I V Q P I I S K L Y G
AGCTGTAGAAGAAAAAGATTGAATGGCTGGAAAGCTCAAGATGCTGACATTGAAGACTTCAAAGCTAAGAAGGAACTGGAAGAAATTGTTCAACCAATTATCAGCAAACTCTATGG 5040
   S  A G P P P T G E E D T A E K D E L *
AAGTGCAGGCCCTCCCCCAACTGGTGAAGAGGATACAGCAGAAAAAGATGAGTTGTAGACACTGATCGTCGCTAGTGCTGTAATATTGTAAATACTGGACTCAGGAACTTTTGTTAGGAAAA 5160
AATTGAAAGAACTTAAGCTCTGAATGTCTCGAATGTAATTGGAATCTTCACCTCAGAGTGAAACTGCTATAGCCTAAGCGCGGCTGTTTACTGCTTTTCATTAGCAGTTGCTCACATGTCTTTGG 5280
GTGGGGGGGAGAAGAAGAATTGGCCATCTTAAAAAGCGGGTAAAAAACCTGGGTTAGGGTGTGTGTTCACCTTCAAAAATGTTCTATTTAACAACTGGGTCATGTGCATCTGGTGTGTAGGAG 5400
GTTTTTTCTACCATAAGTGACACCAATAAATGTTTGTTATTTACACTGGTCTAATGTTTGTGAGAAGCTT
```

| DOMAIN (A) | GIDLGTTYSCV |
| DOMAIN (B) | TVPAYFNDAQRQATKDAGTIAGLNVMRIINEPTAAAIAYGLD |
| DOMAIN (C) | DLGGGTFDVS |
| DOMAIN (D) | FEVVATNGDTHLGGEDFD |
| DOMAIN (E) | VLVGGSTRIPKIQ |
| DOMAIN (F) | NPDEAVAYGAAVQ |
| DOMAIN (G) | LLHVCPLTLGIETVGGVMT |
| DOMAIN (H) | GVPQIEVTF |

FIG. 20A

```
                                                                        -351
HUMAN                                           CCCGGGGTCACTCCTGCTGGA
RAT                                             AACTGACAACGACAAGACCCC
                                                                        -301
HUMAN   CCTACTCCGACCCCCTAGGCCGGGAGTGAAGGCGGGACTTGTGCGGTTAC
RAT     ACTCTCCACTCCCCGGGGGCCCAACGTGAGGGGAGGACCTGGACGGTTAC
                                                                        -251
HUMAN   CAGCGGAAATGCCTCGGGGTCAGAAGTCGCAGGAGAGATAGACAGCTGCT
RAT     CGGCGGAAACGGTTCCAGGTGAGAGGTCACCCGAGGGACAGGCAGCTGCT
             ↑T
                                                                        -201
HUMAN   GAACCAATGGGACCAGCGGATGGGGCGGATGTTATCTACCATTGGTGAAC
RAT     CAACCAATAGGACCAGCTCTCAGGGCGGATGCTGCCTCTCATTGGCGGCC
                                                                        -151
HUMAN   GTTAGAAACGAATAGCAGCCAATGAATCAGCTGGGGGGGCGGAGCAGTGA
RAT     GTTAAGAATGACCAGTAGCCAATGAGTCGGCTGGGGGGGCGTACCAGTGA
                                                                  ↑C
                                                                        -101
HUMAN   CGTTTATTGCGGAGGGGGCCGCTTCGAATCGGCGGCGGCCAGCTTGGTGG
RAT     CGTGAGTTGCGGAGGAGGCCGCTTCGAATCGGCAGCGGCCAGCTTGGTGG
                                                                        -51
HUMAN   CCTGGGCCAATGAACGGCCTCCAACGAGCAGGGCCTTCACCAATCGGCGG
RAT     CATGAACCAACCAGCGGCCTCCAACGAGTAGCGAGTTCACCAATCGGAGG
                                                                         -1
HUMAN   CCTCCACGACGGGGCTGGGGGAGGGTATATAAGCCGAGTAGGCGACGGTG
RAT     CCTCCACGACGGGGCTGGGGGAGGATATATAAGCCGAGTCGGCGACGGCG
                        ↑C                                        ↑C    +50
HUMAN   AGGTCGACGCCGGCCAAGACAGCACAGACAGATTGACCTATTGGGGTGTT
RAT     CGCTCGATACTGGCTGTGACTACACTGAC--TTGGAC-ACTT--GGCCTT
```

FIG. 20B

| RAT | GRP78 | -161 | AATCGGCAGCGGCCA-GCTTGGT | -140 |
| HUMAN | GRP78 | -124 | AATCGGCGGCGGCCA-GCTTGGT | -103 |
| CHICK. | GRP94 | -202 | AATCGACGCCGGCCACGCTCCGT | -180 |

CONTROL OF GENE EXPRESSION BY GLUCOSE, CALCIUM AND TEMPERATURE

This invention was made with government support. The U.S. Government may have certain rights in the invention.

This application is a continuation-in-part of U.S. Ser. No. 282,880 filed Dec. 5, 1988, now abandoned which is a continuation of U.S. Ser. No. 690,951, filed Jan. 1, 1985, now abandoned.

FIELD OF INVENTION

This invention is directed generally to the control of gene expression in eukaryotic cells; it has direct application towards the regulation and control of RNA and polypeptide biosynthesis by recombinant DNA technology.

BACKGROUND

Recombinant DNA technology has advanced to the point where the cloning of select DNA sequences has become possible. According to well known procedures various cohesive DNA fragments can be ligated in vitro to produce powerful expression vectors capable of transforming host organisms to express polypeptide sequences foreign to the host cell. See, Maniatis, T. et al., *Molecular Cloning*, Cold Spring Harbor Laboratory (1982); Cohen et al., U.S. Pat. No. 4,237,224. A generalized discussion of the subject matter appears in S. Cohen, *Scientific American*, 233, 24 (1975). These and other publications alluded to herein are incorporated by reference.

Generally, expression vectors contain DNA encoding a desired polypeptide, an origin of replication, one or more phenotypic selection characteristics and an expression promoter. The expression vector is introduced into its host cells by a process called "transformation" and large quantities of the expression vector are obtained by growing the transformed cells. Where DNA encoding for the desired polypeptide is inserted within reading relationship to the promoter, the mechanisms for the biosyntheses of protein within the host cell transcribe and translate the DNA into polypeptide in a two-step process referred to as "expression."

In the first step, the DNA is enzymatically transcribed in the form of messenger RNA (mRNA) by RNA polymerase. The transcription of DNA is initiated in a region known as the promoter. The promoter contains the RNA polymerase recognition site where the promoter is recognized and bound by RNA polymerase. The promoter sequence itself generally consists of a sequence rich in adeninethymidine base pairs (i.e., TATA) and is not transcribed. Also located 5' to the AT rich sequence is a CAAT sequence which may also be involved in transcription initiation. For a review, see Kessel, M. and Khoury, G., *Gene Amplification and Analysis*, Vol. 3, Papas et al., ed. New York, Elsevier/North Holland, Inc. 1983, pp. 234–266.

Soon after binding to RNA polymerase recognition site, RNA polymerase begins to diffuse down the DNA sequence. Eventually the RNA polymerase will encounter the transcription start site at which point the RNA polymerase begins to transcribe mRNA from the DNA sequence coding for the polypeptide. The DNA sequence encoding the polypeptide is referred to as the "structural gene". In the second step, the mRNA is translated into a polypeptide having the amino acid sequence for which the structural gene codes.

Expression of certain polypeptides is regulated at the point of transcription by certain "regulatory sequences." In procaryotic systems, expression of certain sets of genes has been shown to be regulated by operator, promoter and attenuator sequences. These sequences are located at the 5' end of the structural genes. For example, the lactose operon of *E. coli* contains an operator. An operator is a DNA sequence which is recognized by repressor proteins. The repressor binds to the operator and thereby sterically prevents RNA polymerase from binding to the adjacent promoter or diffusing down the DNA sequence. The repressor therefore has the ability to shut off expression of the particular gene. A substance called the "inducer" deactivates the repressor, freeing the operator and permitting RNA polymerase to bind to the promoter.

The tryptophan (trp) operon of *E. coli* is another example of an inducible system. The trp operon is repressed by tryptophan, which binds to the specific repressor and thereby enables it to interact with the operator. The effect is to switch off the transcription of the genes that code for the biosynthesis of tryptophan. Chang et al., *Nature*, 275, 615 (1978); Itakura, et al., *Science*, 198 (1977); Goeddel, et al., *Nucleic Acids Res.*, 8, 4057 (1979). Several operons for the biosynthesis of amino acids, including the trp operon, are also controlled by an attenuator site. Transcription terminates at this site if the amino acid end product is abundant. Jacob and Monod, *J. Mol. Biol.*, 3, 318–356 (1961); Miller and Reznikoff, The Operon, Cold Spring Harbor Laboratory (1978); Chang et al., *Nature*, 275, 615 (1978).

Inducible systems are also found in eukaryotics. One example is the yeast repressible acid phosphatase (A. Pase) gene, pH05. Schurr and Yagil, *J. Gen. Microbiol.*, 65, 291–303 (1971). Transcription of the pH05 gene is tightly repressed when inorganic phosphate is present in the growth medium but is induced to high levels when inorganic phosphate is depleted. Bostian et al., *Proc. Natl. Acad. Sci. U.S.A.*, 77. 4504–4508 (1980).

The regulatory/promoter sequences of these procaryotic operon systems as well as the yeast systems have been introduced into expression vectors to direct the synthesis of polypeptides under induced and non-induced conditions in *E. Coli* host cells or yeast *saccharomyces cerevisiae* systems. See, e.g., Kramer, R. A. et al., *Proc. Natl. Acad. Sci. U.S.A.*, 81, 367–370 (1984). These regulatory/promoter sequences, although useful in procaryotes and lower eucaryotes such as the yeast, are not always applicable for higher eukaryotic host systems, such as mammalian tissue culture cells.

In recent years, the availability of cloned genes and methods by which they are transferred into eukaryotic cells, has made it possible to identify similar regulatory sequences in animal cells. For purposes of the present invention, the term "regulatory sequences" refers to the regulatory sequences which are required for transcription regulation of a gene system and may or may not include a promoter sequence.

The experimental approach towards the investigation of such regulatory sequences falls into two categories. In both cases, hybrid genes consisting of a putative control region from the inducible gene and the structural gene sequences coding for drug resistance or a enzymatic activity are constructed. In one approach, these hybrid genes are transfected into tissue culture cells and single-cell clones which have integrated these hybrid genes into their chromosomes are grown up under selective conditions. To demonstrate the inducibility of these integrated genes, expression in the presence and absence of the inducible agent is evaluated by RNA analysis or by direct measurement of the protein product of the inducible gene. In the second approach, the hybrid gene is simply introduced into the eukaryotic cell of interest. Shortly after transfection (generally several hours to a few days) an extract is made of the cultures, which have been maintained in the presence or absence of inducer. The extract is then analyzed for the gene products (RNA or protein).

These methods have been used successfully to locate specific eukaryotic regulatory sequences. Examples are mouse and human metallothionein genes which are inducible by heavy metals [Mayo et al., Cell, 29, 99–108 (1982), Karin et al., Cell, 36, 371–379 (1984)]and the Drosophila heat shock regulatory sequence which is inducible by heat [Pelham, Cell, 30, 517–528 (1982)]. Other regulatory sequences are isolated from viral sources such as the SV40 early promoter/enhancer and that of the mouse mammary tumor viruses. Lee F., et al., Nature, 294, 228–232 (1981).

Inducible regulatory sequences are useful in the area of recombinant DNA technology. These regulatory sequences can be inserted into recombinant DNA expression vectors for the controlled expression of a desired gene. Inducible regulatory sequences are particularly useful when the desired polypeptide is toxic to the host cell. When the polypeptide is toxic to the host cell the cell will be unable to replicate in any significant amount. An inducible regulatory sequence can be used to shut off expression of the toxic polypeptide until the host cells are replicated. Once a desired amount of host cells are obtained the regulatory sequence can be activated by varying culture conditions, thus enabling large quantities of the peptide to be produced.

The regulatory sequence of the present invention is another example of a mammalian regulatory sequence. It has the unique ability to enhance transcription under conditions of glucose starvation or calcium shock in a variety of eukaryotic host systems. The regulatory sequence can also enhance transcription by high temperature when introduced into the temperature-sensitive Chinese hamster cell line K12 or other systems having a compatible mutation.

SUMMARY OF THE INVENTION

A novel regulatory sequence capable of enhancing RNA or polypeptide biosynthesis under conditions of glucose starvation, calcium shock, or high temperature is provided along with a method for its use. The regulatory sequence of the present invention can be inserted into expression vectors containing the DNA sequence of a desired polypeptide to form a hybrid gene. The resulting hybrid gene containing expression vector can be used to transform a variety of host systems.

When the regulatory sequence of the present invention is inserted within reading relationship of the desired polypeptide's structural DNA, transcription of the polypeptide's structural gene can be enhanced to high levels by glucose starvation or calcium shock. Transcription can also be enhanced by high temperature when the hybrid gene containing expression vector is used to transform a temperature sensitive hamster cell line of Chinese hamster cells, or any other ts mutant which contains a compatible mutation.

Other aspects and advantages of the invention should become apparent from the following detailed description of the invention, taken in conjunction with the accompanying drawings, which illustrate, by way of example, the principles of the invention.

BRIEF DESCRIPTION OF THE DRAWINGS

FIG. 2 shows the nucleotide sequence of the regulatory sequence of the rat 78-kilodalton glucose regulated protein taken from the 0.342 kb SmaI/BsshII fragment of the RAT 1 genome. The TATA initiation site is indicated.

FIG. 15 shows the processed pseudogene from clone hu 3-2B and the sequence surrounding the insertion site. A. The lower line shows the restriction map of the 15-kb human genomic DNA insert within the phage. The upper line shows the expanded region spanning the 4.4-kb Pst I fragment containing GRP78 coding sequences (black box) and untranslated regions (open boxes). The restriction sites marked are Ava I (A), Apa I (Ap), Bam HI (B), Bgl II (Bg), Bst EII (Bs), Cla I (C), Eco RI (E), Hae II (Ha), Nae I (Na), Nco I (Nc), Nde I (Nd), Pvu II (Pv), Pst I (P), Sac I (Sa), Xba I (X). B. the nucleotide sequences immediately surrounding the pseudogene. The 13-nucleotide direct repeat sequence flanking the inserted gene is marked by arrows.

FIG. 17 shows the primary structure of the human GRP78 gene. The DNA sequence is determined from lambda clone hu28-1. The intronexon boundaries were mapped by comparison with the rat and hamster cDNA sequences (Ting et al., 1987). The GT-AG exon-intron boundaries are indicated by boldface. The TATA and poly(A) addition sequences are underlined. The bent arrow indicates the major transcriptional start site. The termination codon TAG is indicated by a star. The amino acid sequence is shown in the one-letter code. Black triangle indicates the proteolytic cleavage site that excises the 18-amino-acid leader sequence and produces the amino terminus of the mature protein.

FIG. 20 is a sequence comparison between the human and the rat GRP78 promoter. A. The promoter sequence of rat and human GRP78 gene reported here are aligned to obtain maximal homology. The sequence is numbered starting from the major RNA cap site (bent arrow) of the human GRP78 gene as +1. Identical nucleotides are indicated by vertical dots. The TATA and CCAAT sequences are boxed. The putative Spl binding sites are underlined. The deletion end points of the two GRP78-CAT fusion genes tested (−368 and −170) are indicated (inverted black triangle). B. The consensus sequence found in the promoter regions of the human, rat GRP78 gene and the chicken GRP94 gene. The sequences are numbered starting from their RNA initiation site. The location of this sequence in the human and rat GRP78 promoter is marked by a heavy line in A.

DETAILED DESCRIPTION OF THE INVENTION

Figure 1:
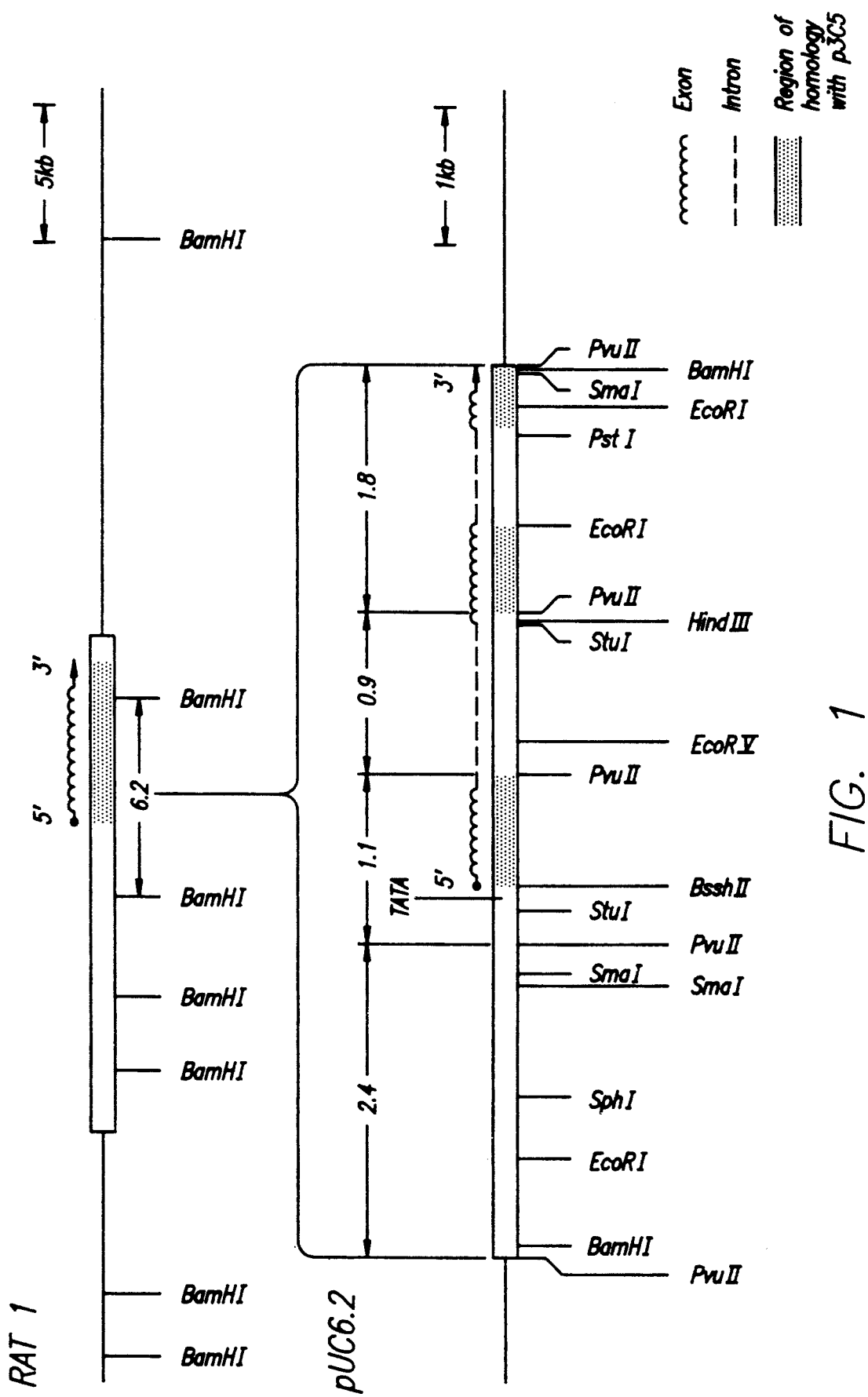
FIG. 1 shows a schematic diagram of the rat geonomic clone RAT 1. The 5' region of the RAT 1 gene was isolated from a rat charon 4A recombinant phage library. The RAT 1 gene was further defined by subcloning a 6.2 kb BamHl fragment into the BamHl site of pUC8. The relative positions of the various restriction endonuclease cleavage sites and direction of transcription are depicted. Fine restriction mapping and hybridization of the PvuII subfragments 2.4, 1.8, 1.1, and 0.9 kb (kilobase) with p3C5 and cDNA probes made from rat mRNA showed transcription initiated about 2.8 kb from the left BamHl site. The location of the promoter (TATA) sequence was determined by DNA sequencing.

The recombination of genes is an effective method for freeing the expression of certain polypeptides from the transcriptional dictates contained within the regulatory sequence of the native genome. This is accomplished by inserting the DNA sequence of a desired polypeptide within reading relationship of an inducible regulatory sequence. Expression of the polypeptide sequence then becomes inducible under conditions where the native genome is not. In this way transcription of the hybrid gene can be induced under conditions which would normally not cause expression in the native host.

The present invention provides an isolated nucleic acid comprising the regulatory sequence of a gene encoding a glucose regulated protein and methods for its use. Fragments of the regulatory sequence which can effect transcription are also provided. Such fragments are readily ascertainable by a person skilled in the art. The regulatory sequence was derived from the rat and human genome encoding for the 78,000 dalton glucose-regulated protein (GRP). GRPs are a set of proteins synthesized in various animal cell lines when glucose in the growth medium is depleted. Shiu et al., *Proc. Natl. Acad. Sci. U.S.A.*, 74, 3840–3844 (1977); McCormick et al., *Cell*, 18, 173–182 (1979); Welch et al., *J. Biol. Chem.*, 258, 7102–7111 (1983); Lee et al., *J. Biol. Chem.*, 259, 4616–4621 (1984). There are currently three known GRP having weights of 94, 78 and 58 kilodaltons. The 78 kilodalton GRP may vary in molecular weight from 78-80 kilodaltons. For purposes of the present invention, the term "78-kilodalton" GRP shall mean the GRPs having a molecular weight of approximately 78-80 kilodaltons. The 78-kilodalton protein (GRP78) is the most abundant GRP in chicken, hamster, rat, mouse, and human cells.

The GRPs are cellular proteins synthesized constitutively at low but detectable amounts under normal tissue culture conditions, but their synthesis is markedly enhanced in response to glucose starvation. Recent reports also establish that the same set of proteins are induced in a large variety of cell lines by treatment of the cells with calcium ionophores, ionomycin or A23187, or by changing the $Ca^{2+}$ concentration of the culture medium. Wu et al., *J. Biol. Chem.*, 256, 5309–5312 (1983); Welch et al., *J. Biol. Chem.*, 258, 7102–7111 (1983); Lee et al., *J. Biol. Chem.*, 259, 4616–4621 (1984); Martonosi et al., *Ann. New York Acad. Sci.*, 402, 485–514 (1982).

GRPs are also induced at non-permissive temperature in the temperature-sensitive mutant K12, derived from Chinese hamster fibroblasts. A. S. Lee, *J. Cell Physiol.*, 106, 119–125, 1981. There is also a corresponding increase in the level of cytoplasmic mRNA encoding for GRP. Lee et al., *J. Biol. Chem.*, 258, 597–603, 1983; Lin and Lee, *Proc. Nat. Acad. Sci. U.S.A.*, 81, 988–992 (1984). Thus, under normal conditions, GRP78-mRNA comprise about 0.1% of the total cytoplasmic polyadenylated RNA (polyA-RNA). However, when K12 cells are deprived of glucose at 35° C. or shifted to 40° C. in normal culture media, there is a tenfold increase in the GRP78-mRNA. Further, when K12 cells are treated with calcium ionophore A2318, the amount of GRP78-mRNA increases up to thirtyfold.

The GRP regulatory sequence resides within the 5' flanking sequence of the GRP genome. As shown in FIG. 1 the GRP regulatory sequence is flanked on its 3' end by the TATA initiation sequence and the GRP78 structural gene. The DNA sequence of the GRP78 regulatory sequence extending from the SmaI to the BsshII site is set forth in FIG. 2. The GRP regulatory sequence is characterized by its ability to enhance RNA or polypeptide biosynthesis to high levels under conditions of glucose starvation, calcium shock or high temperature.

From deletion analysis, a 1.1 kb fragment containing the TATA sequence and its flanking sequence (FIG. 1) contains the regulatory sequence for the induction by calcium, temperature and glucose starvation. A 1.3 kb fragment 5' to the BsshII site (FIG. 1) contains sufficient information for the induction of the regulatory sequence by calcium and temperature. In addition, a 0.292 kb fragment can be excised from the 6.2 kb BamHI fragment by digestion with the restriction endonuclease StuI and SmaI. This fragment has the property of an eukaryotic enhancer in that it can enhance transcription of a downstream promoter irrespective of its location to the promoter. When this fragment is inserted in front of another promoter, it increases the basal rate of transcription under non-induced conditions, and it further stimulates transcription under glucose starvation or calcium shock.

The ability of the GRP regulatory sequence to enhance RNA or polypeptide synthesis under select conditions makes it particularly useful in the field of recombinant DNA technology. The GRP regulatory sequence is a non-viral regulatory sequence which is useful in a wide variety of host systems including Chinese hamster cells. These cells are particularly useful in large scale polypeptide production due to their ability to grow in culture medium without costly serum.

Thus, in large scale preparation of protein, the GRP regulatory sequence can be used to enhance transcription to high levels by simply starving the altered cells of glucose. A further advantage of the GRP regulatory sequence is realized where the selected protein is toxic to the host cell in high concentrations. In such cases, the synthesis of the toxic protein is held to moderate levels by the GRP regulatory sequence while the transformed cells are incubated in normal glucose-containing medium at normal temperature. The cells are thus able to grow uninhibited by the presence of the toxic protein. After a desired amount of cells are obtained, the glucose is depleted from the medium or the cells are calcium shocked thereby inducing the synthesis of the toxic protein to high levels. The expression of the toxic protein can also be controlled by temperature when K12 cells are used. In this manner, synthesis of the toxic protein occurs only after large amounts of the transformed cells have been obtained.

Accordingly, in one embodiment of the invention the GRP regulatory sequence is inserted into plasmid having DNA encoding for the desired polypeptide. The plasmid is in turn used to transform a host cell. Suitable host cells can include a variety of eukaryotic cell lines. Preferably cell lines which can express endogenous GRP are used. Most preferred are cell lines from chicken, hamster, rat, mouse, and human origin. Examples of such cell lines include the Chinese hamster fibroblast cell lines WglA and K12, Chinese hamster ovary cells (CHO), the human embryo kidney fibroblast cell line 293, mouse L cells, rat kidney fibroblast cells (NRK) and chicken embryo fibroblast.

Stable transformants are selected for their ability to express the desired polypeptide. The specific procedure for assaying the expression of an individual polypeptide will vary depending upon the polypeptide's characteristics. The transformed cells are allowed to grow in glucose containing medium at normal temperatures. After a desired amount of cells have ben achieved, a glucose-free growth medium is substituted from the glucose-containing medium. Alternatively, when the density of the cell culture increases as a consequence of cell growth, the culture medium will automatically be deprived of glucose because of cell uptake and utilization. Therefore, as soon as the level of glucose has dropped in the culture medium, the GRP regulatory sequence will be induced. Addition to 10 mM of glucosamine to normal medium will also mimic the effect of glucose starvation. Lee, A. S., *J. Cell Physiol.*, 106, 119–125 (1981). Within 8 to 12 hours of glucose deprivation, newly synthesized mRNA of the selected polypeptide will be observed. These levels will increase up to tenfold during the course of incubation. The cells are then harvested for the desired polypeptide.

Induction of selected RNA or plypeptide synthesis can also be accomplished by methods of calcium shock. Thus, according to the present invention, cells are transformed by the GRP regulatory sequence containing plamid and grown in glucose-containing medium at normal temperature until a desired amount is obtained. At that time, calcium ionophores such as A23187 are added. A final concentration of 7 µM is preferred. Alternatively, the cells can be shifted to a growth medium low in calcium concentration. A calcium concentration of less than 0.15 mM is preferred. The cells can also be shocked by growing them in medium low in calcium and then shifting into a growth medium containing normal calcium levels ranging between 1.8–5 mM.

Within three hours of the ionophore treatment, the induced synthesis of mRNA encoding for the selected polypeptide will occur and will increase thirtyfold throughout the incubation period.

Similarly, induction of selected RNA or polypeptide synthesis can be accomplished by treatment of recipient cells with B-mercaptoethanol (0.25% for 12 hr.) as described by Kim, K. K. and Lee, A. S. *Mol. Cell. Bio.* 7:2974–2976 (1987).

Another advantage of the GRP regulatory sequence is its ability to induce RNA or polypeptide synthesis by altering temperature. In this procedure, the GRP regulatory sequence containing plasmid is used to transform the ts mutant of Chinese hamster fibroblast K12. Roscoe et al., *J. Cell Physiol.*, 82, 325–332, 1973); Milcro, J. A., Fincham, V., *J. Cell Physiol.*, 95, 295–306 (1978) Lee, A. S., *J. Cell Physiol.*, 106, 119–125 (1981). The K12 cells incubated at normal temperature in glucose containing medium until the desired amount of cells are obtained. At this point, the incubation temperature is shifted to the nonpermissive temperature of 39.5–40.5° C. Within two hours of the temperature shift, a marked increase in the mRNA encoding for the selected polypeptide will occur. These levels will increase up to tenfold throughout the incubation period.

The GRP regulatory sequence can be inserted into the plasmid along with its 3' coding sequence and still remain functional. Thus, the entire 6.2 kb BamHl fragment can be inserted upstream to the coding sequence of the selected polypeptide and the GRP regulatory sequence will still enhance polypeptide synthesis. Since the 3' flanking sequence of the GRP regulatory sequence contains the structural gene for GRP78 the resulting polypeptide sequence will be a hybrid between GRP78 peptide and the desired peptide. The GRP peptide sequence can be removed by well known techniques depending upon the nature of the hybrid peptide.

Preferably, the GRP regulatory sequence is inserted free of its 3' coding upstream to the coding sequence of the selected polypeptide. In this way the resulting hybrid gene contains only the structural gene of the desired polypeptide. Accordingly, the need to further process the desired polypeptide after synthesis to rid it of an additional peptide sequence is eliminated. Examples of regulatory sequences free of the 3' structural gene sequences include the 1.3 kb BsshII sequence of pI10 (described in more detail in Examples XII–XIII below) and the 0.292 StuI/SmaI fragment (Examples X and XI).

Figure 8:
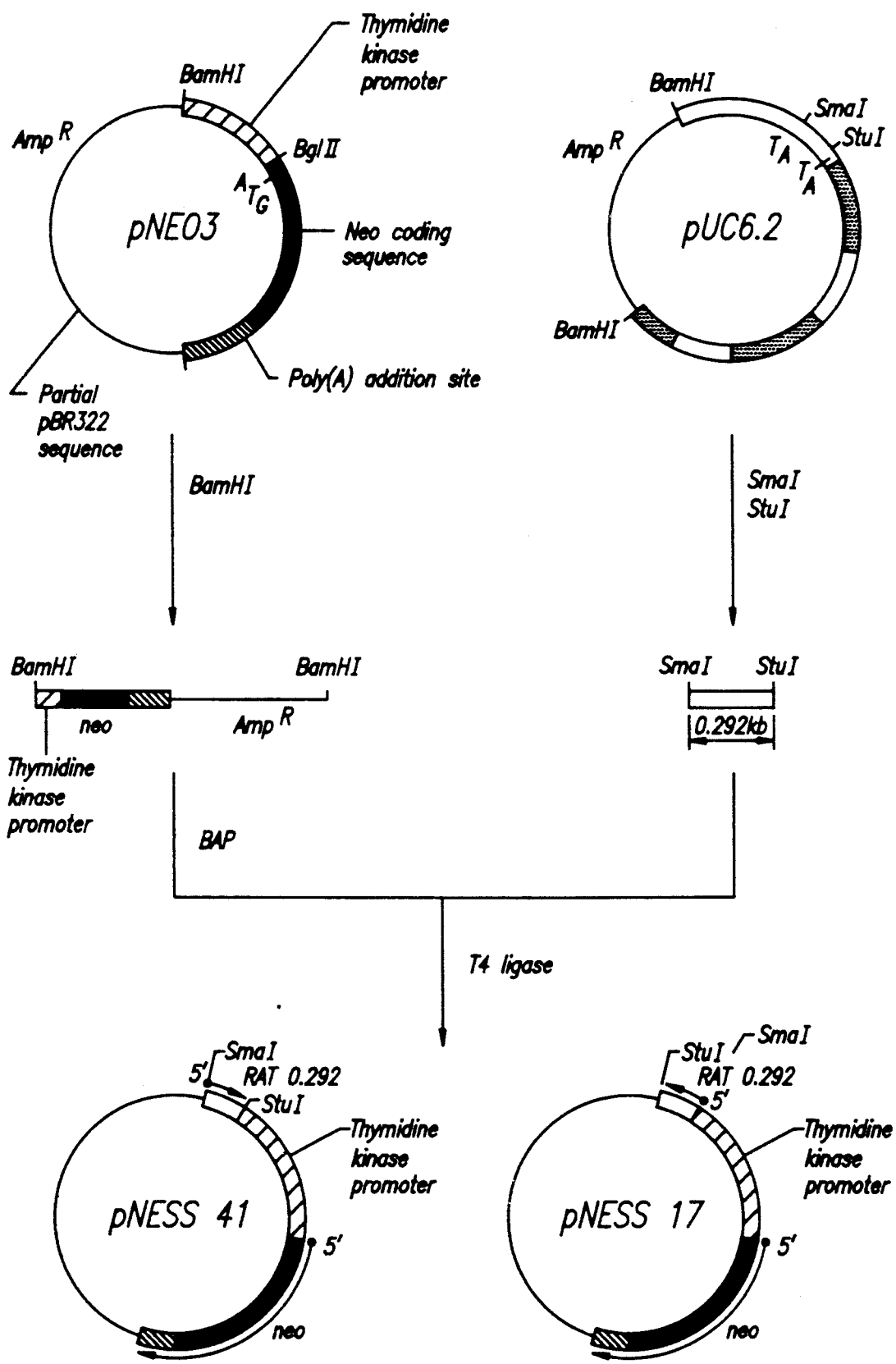
FIG. 8 shows a flow chart for the construction of plasmids pNESS17 and pNESS41. The relative positions of the endonuclease sites used in the procedure as well as the Amp$^R$, neo and restriction site flanking the thymidine kinase promoter are depicted as in FIG. 3. Digestion of pUC6.2 with SmaI and StuI yields a 0.292 kb fragment which is missing the TATA sequence of the RAT 1 gene. The orientation of the RAT 0.292 sequence with respect to the neo gene was determined by restriction analysis. Both pNESS17 and pNESS41 contain the thymidine kinase promoter of the parent pNE03 plasmid.
Figure 9:
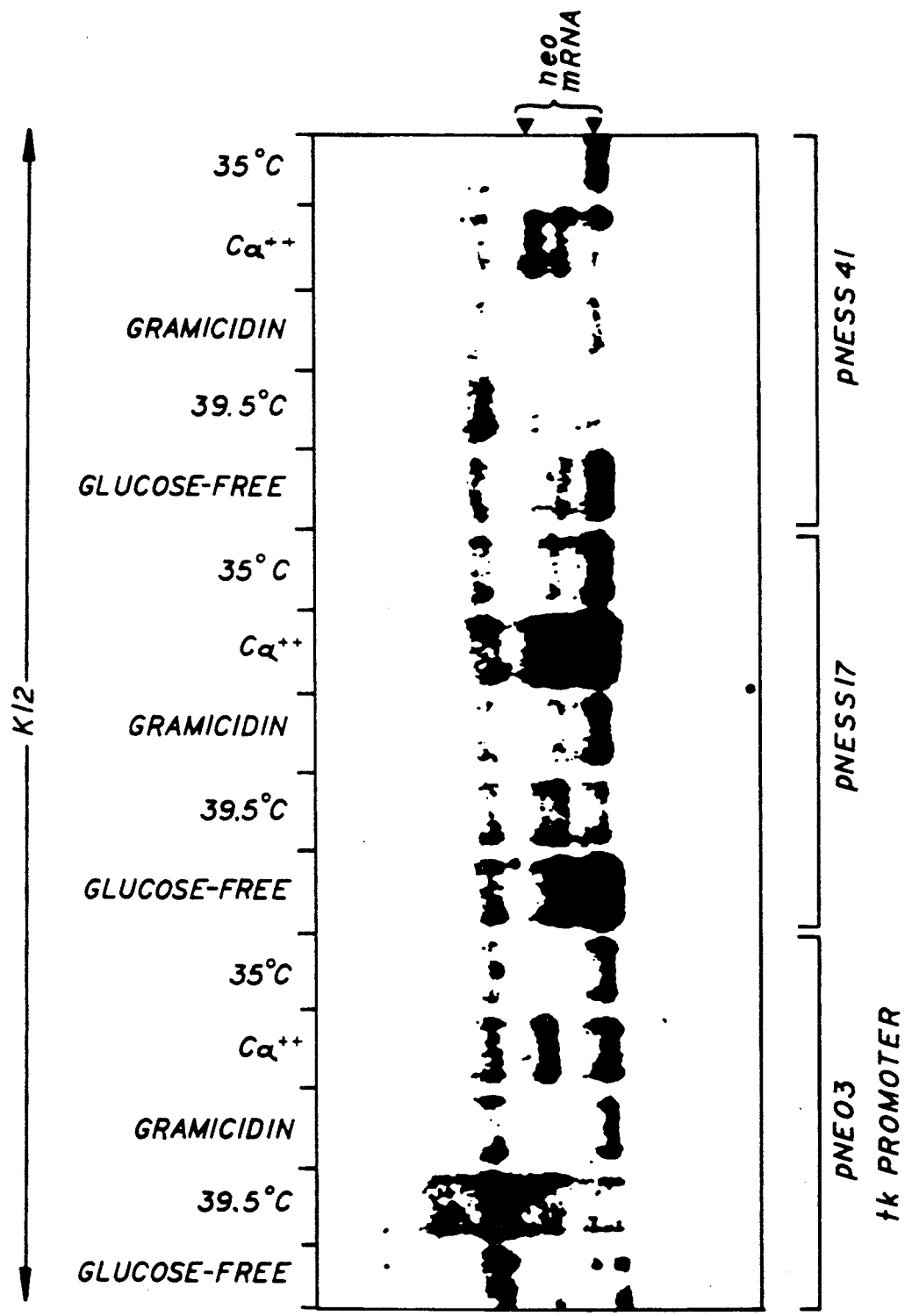
FIG. 9 is an autoradiogram showing the level of neo-mRNA transcribed by stable pNESS17 and pNESS41 transformants of the K12 cell line under conditions of glucose starvation, calcium shock, or high temperature.

In another embodiment of the invention the GRP regulatory sequence can be further digested by the restriction endonuclease SmaI and StuI to yield a fragment free of the TATA initiation sequence (FIG. 8). The resulting StuI/SmaI fragment is capable of enhancing polypeptide transcription under conditions of glucose starvation and calcium ionophore treatment but not high temperature. As demonstrated in Example XII the 0.292 kb SmaI/StuI fragment is capable of enhancing transcription of the desired polypeptide in either transcriptional orientation (FIG. 9). The ability of the 0.292 kb SmaI/StuI fragment to operate in this fashion eliminates the need for selecting transformants in which the GRP regulatory sequence is inserted in the same transcriptional orientation as the structural gene.

Since the 0.292 kb SmaI/StuI fragment is missing its own TATA promoter sequence, a TATA sequence from another regulatory sequence can be used. The resulting hybrid regulatory sequence can be inserted into a suitable expression vector for the transformation of host cells. The 0.292 kb SmaI/StuI hybrid regulatory sequence has a number of distinct advantages. The hybrid regulatory sequence can contain a non-GRP promoter (i.e. the thymidine kinase promoter of Example XII.) which may be more readily recognized by the RNA polymerase of the host cell than the GRP promoter. Accordingly, the 0.292 kb SmaI/StuI sequence can be inserted upstream to large variety of different promoter sequences in order to further enhance transcription.

EXPERIMENTAL

The following vectors are merely examples of effective vectors useful in the subject invention. Generally, the specific plasmids are either publically available or capable of creation by one skilled in the art.

The pBR322 Plasmid

The plasmid pBR322 is well characterized and widely available. The plasmid has a molecular weight of approximately 2.6 megadaltons and carries genes coding for ampicillin ($Amp^R$) and tetracycline (Tc) resistance. The construction of pBR322 has been fully described in Bolivar et al., Gene, 2, 95–113 (1977).

The pUC8 Plasmid

Plasmid pUC8 is approximately 2.7 kb in length and contains the 2297 bp EcoRI/PvuII DNA fragment of pBR322 which includes the gene coding for ampicillin resistance. Sutcliffe, *Nucleic Acids Res.*, 5, 2721 (1978). The PstI and HindIII sites of pBR322 are altered by single base pair changes to destroy the restriction sites while retaining B-lactamase activity and the AccI site has been removed by BAL-31 treatment. A modified 424 bp HaeII fragment from M13 mp8 and mp9[3] has been inserted between the EcoRI and PvuII sites. This modified fragment contains a portion of the lac operon and a 33 bp insert (which replaces the 42 bp multiple cloning region of mp[7]) and includes restriction sequences for EcoRI, XmaI, SmaI, BamHI, SalI, AccI, HindII, PstI and HindIII. The order of these restriction sites in pUC8 is in the direction of transcription. The detailed construction of pU8 has been described (C. Vieira and J. Messing, *Gene*, 19, 259, 1982).

The oNE03 Plasmid

The pNE03 plasmid was provided by Dr. B. Wold. The plasmid contains the neomycin resistant coding sequence inserted into @.he BamHI and PvuII site of pBR322 (B. Wold, R. Sweet, R Axel, personal communication). The expression of the neo gene (1.2 kb) is regulated by the Herpes thymidine kinase promoter contained within a 0.68 kb BamHI/BglII fragment previously described in S. L. McKnight and E. R. Gavies, *Nucleic Acids Res.*, 8, 5931 (1980).

The pSVOCAT Plasmid

The pSVOCAT plasmid was provided by Dr. B. Howard. The plasmid contains the bacterial chloramphenicol acetyl transferase (CAT) gene inserted into the pBR322 sequence. The CAT gene is 5' to the HindIII site where promoter sequence can be inserted. Detailed description of this plasmid is published in Gorman et al., *Mol. Cell. Bio.*, 2, 1044–1051 (1982).

The pSV2CAT Plasmid

The pSV2CAT plasmid was provided by Dr. B. Howard. It contains the pSVOCAT sequence, with the entire SV40 early promoter. Southern, P. J. and Bert., *J. of Mol. and Applied Genetics*, 1, 327–341 (1982).

The pMKCAT Plasmid

The pMKCAT plasmid was provided by Dr. M. Karin. It contains the pSVOCAT sequence, with 0.77 kb of the human metallothionien II gene promoter inserted 5' to the CAT gene. Karin, et al., *Cell*, 36, 371–379 (1984).

The p3C5 Plasmid

The plasmid p3C5 has been previously described in A. S. Lee et al., *Proc. Natl. Acad. Sci.*, 78, 4922 (1981). The plasmid contains a complementary DNA (cDNA) sequence encoding for GRP78. The GRP78-DNA sequence was obtained by treatment of GRP78-mRNA produced by the ts K12 mutant at the non-permissive temperature of 40.5° with reverse transcriptase. The plasmid p3C5 was constructed according to the following procedure.

Synthesis of GRP78 cDNA

K12 cells were grown to confluence at 35° C. and incubated at 40.5° C. for 16 hours. Cytoplasmic RNA was isolated according to the procedure of Harpold et al., *Cell*, 17, 1025 (1979). The poly(A)+RNA fraction was prepared by chromatography on oligo(dT) cellulose. The poly(A)+RNA was used as a template for DNA synthesis, according to the procedure of Efstradiatis et al., *Cell*, 4, 367–378 (1975). The cDNA reaction solution consisted of 50–100 µg/ml poly(A)+ RNA, 10 mM MgCl$_2$, 80 mM KCl, 50 mM Tris-HCl, pH 8.3, 1 mM each of dTTP, dATP, dGTP and dCTP, 20 µg/ml Actinomycin D, 20 µg/ml oligo dT$_{12-18}$ primer (P-L Biochemicals, Milwaukee, Wis.), 30 mM 2-mercaptoethanol and 500 units/ml reverse transcriptase (P-L Biochemicals, Milwaukee, Wis.). About 1.4×10$^7$ cpm of H$^3$dTTP was added for the purpose of monitoring the incorporation. Incubation was at 42° C. for 20 minutes. To stop the reaction, SDS was added to 0.4% and EDTA to 10 mM. The mixture was extracted once with phenol and once with chloroform. Following three minutes incubation at 50° C., the mixture was applied onto a Sephadex G-150 column in a 10 ml plastic disposable pipette, equilibrated with 50 mM HEPES, pH 7.6, 1 mM EDTA and 0.5 ml fractions were collected. The exclusion peak, detected by the H$^3$dTTP incorporation into the cDNA, was pooled. Yeast tRNA (30 µg) was added as carrier and the pooled fractions were adjusted to 0.3M NaOAc pH 5.4 and precipitated at −20° C. by addition of two volumes of 95% ethanol. This poly(A)RNA-cDNA hybrid was subsequently tailed with oligo(dA) with terminal transferase and inserted into the BamHI site of pBR322.

Insertion of GRP78 cDNA into pBR322

The plasmid pBR322 was tailed with oligo(dT) according to the procedure of Roychoudhry et al., *Nucleic Acids Res.*, 3, 101 (1976). Ten micrograms of pBR322 was cleaved with BamHI in the 10× TA buffer (1× = 66 mM KAc, 10 mM MgCl$_2$, 33 mM Tris, pH 7.5, 0.5 mM DTT). After phenol extraction and alcohol precipitation, the DNA was tailed with dTTP. The tailing reaction solutions contained 1× cacodylate buffer (1× = 0.14 M Na cacodylate, 0.03 M Tris, 0.1 mM DTT, pH 7.6), 1 mM 2-mercaptoethanol, 1 mM CoCl$_2$, 3 µg of BamHI cut pBR322 DNA, and 0.1 mM dTTP (about 5×10$^5$cpm of H$^3$dTTP was added to monitor the incorporation). Preincubation was carried out at 37° C. for 10 minutes and 45 units of terminal transferase (PL Biochemicals) was added. The solution was further incubated at 37° C. for 14 minutes. The reaction was stopped by addition of 0.4% SDS and 10 mM EDTA. From the amount of H$^3$TTP incorporated, it was calculated that every pBR322 molecule had an average of 500 nucleotides of thymidine at its 3' end. The BamHI site and the tetracycline-resistance gene were destroyed when the dT residues were tailed to its 3' end.

The poly(A)+RNA-cDNA was tailed by a method similar to that described for the tailing the vector pBR322. The reaction volume was 75 containing 1× cacodylate buffer, 0.1 mM dATP (about 6×10$^6$cpm of a P$^{32}$ dATP was added to monitor the incorporation), 1 mM 2-mercaptoethanol, 2 mM CoCl$_2$ and 1 µg of RNA-cDNA hybrid. Preincubation was at 37° C. for ten minutes. The reaction was started by the addition of 27 units of terminal transferase (PL Biochemicals). After one hour of incubation at 37.C, the reaction was stopped by addition of 0.4% SDS and 10 mM EDTA. The amount of residues attached to the 3' end of the Poly(A) RNA-cDNA hybrid was estimated to be 20 nucleotides.

The two samples containing the tailed plasmid pBR322 and poly(A) RNA-cDNA hybrid were mixed and applied to a G50 column. The column was washed with buffer containing 0.3 M NaCl, 10 mM Tris, pH 7.4, 1 mM EDTA and 0.05% SDS. The exclusion peak, as detected by α $P^{32}$ and $H^3$cpms, was pooled. Yeast tRNA (20 μg) was added and the fractions were alcohol precipitated. The DNA was resuspended in 30 lambda of reannealing buffer which contained 0.1 M NaCl, 10 mM Tris, pH 7.4 and 0.2 mM EDTA. The mixture was heated at 65° C. for three minutes and reannealed at 40° C. for two hours. The solution was cooled on ice until transformation.

Transformation

Transformation was by the procedures of Kushner, S. R., *Genetic Engineering*, eds., Boyer, H. W. and Nicosia, S. (Elsevier, Amsterdam), pp. 17-23 (1978). *E. coli* HB101 was streaked out on Luria agar plate (L plate) on day preceding experiment. For each transformation, 10 ml of expotentially growing HB101 was used. After centrifugation, the cells from a 100 ml culture were suspended in 10 ml of 100 mM MOPS, pH 6.5, 50 mM $CaCl_2$ and 10 mM $RbCl_2$ and kept on ice for 30 minutes. After centrifugation at 8000 rpm for ten minutes, the cell pellet was resuspended in 1.2 ml of the same buffer and 18 lambda of DMSO was added. After 30 minutes on ice, the tailed DNA-cDNA pBR322 hybrid was added to the bacteria. The RNA cDNA hybrid, originally resuspended in 30 lambda of reannealing buffer, was adjusted to 10 mM MOPS by addition of 3 lambda of 0.1 M MOPS, pH 7.0. The solution was split into two fractions, and each fraction was added to 0.5 ml of the above bacterial suspension. After 25 minutes on ice, the cells were incubated at 40.5° C. for 30 seconds and 3 ml of Z broth (1.6 g nutrient broth, 1.0 g peptone, 0.2 g glucose and 100 ml $H_2O$, pH 7.5) was added. Incubation was continued at 37° C. for 50 minutes. At that time, the transformants were plated with 0.8% overlay agar containing 60 μg/ml ampicillin. After 16 hours at 37° C., the ampicillin resistant transformants were visible. A total of about 500 cDNA clones were obtained for 400 ng of hybrid DNA and 90% of the recombinants contained recombinant plasmids.

Screening for GRP78 cDNA Transformants

The cDNA clones were screened for sequences differentially expressed by K12 cells at 40.5° C. by the colony hybridization procedure as essentially described in Lasky et al. *Proc. Natl. Acad. Sci. U.S.A.*, 77, 5317 (1980). The cDNA transformants were grown up in microtitre plates. Millipore nitrocellulose filters were placed onto L plates containing appropriate antibiotics, and the entire microtitre arrays were transferred onto filters simultaneously using a replica plating device (Weiss, B., and Milcarek, C. (1974), *Methods in Enzymology*, 79, 1980). Colonies were grown up at 37° C. overnight after which nitrocellulose filters containing colonies were transferred to L plates containing 200 μg/ml chloramphenicol. Colony filters were incubated on chloramphenicol plates for 12-24 hours to amplify plasmid signals.

The colonies were lysed and the DNA fixed in situ by laying nitrocellulose filters, colony side up, onto Whatmann 3 mm filters soaked for five minutes each in fixing solution containing 0.5 M NaOH, 0.5 M Tris, pH 7.4, 0.5 M Tris, pH 7.4, and 1.5 M NaCl. Filters were air dried, rinsed in 0.3 M NaCl, air dried, then baked at 80° C. for 2-4 hours in a vacuum oven.

The filters were washed at 68° C. for 2-4 hours in 10×Denhardt's solution (50×1% BSA, 1% polyvinyl prolidone, 1% Ficoll, 1% SDS). Filters were then prehybridized for one hour at 68° C. in hybridization juice 4X SET (3 M NaCl, 0.6 M Tris, pH 8, 0.04 M EDTA), 5X Denhardt's, 0.1% NaPPi, 0.025 M phosphate buffer (pH 6.8), 50 μg/ml sheared DNA, 50 μg/ml poly rA, 50 μg/ml poly rC). Filters were then hybridized to $P^{32}$-labeled probe in hybridization juice at 68° C. for 16 hours.

After hybridization filters were washed at 68° C. 3 times in 1×SET, 5X Denhardt's, 0.1% NaPPi, 0.025 M phosphate buffer for 30 minutes each. They were then washed 3 times in 0.1X SET, 0.1% NaPPi, 0.025 M phosphate buffer, 0.1% SDS for 30 minutes each. Filters were air dried, covered with Saran Wrap and exposed with X-ray film with an intensifying screen at −70° C. for 1 to 2 days.

The $P^{32}$-labeled probes used for the differentially screening were radioactive cDNA made using poly(A) RNA extracted from K12 cells incubated at 40.5° C. for 16 hours or 35° C. for 16 hours as templates. To prepare radioactive cDNA, the reaction volume was 25 lambda and contained 0.5 μg of poly(A) RNA, 10 mM $MgCl_2$, 80 mM KCl, 50 mM Tris, pH 8.3, and 1 mM each of dTTP, dATP and dGTP, 20 μg/ml actinomycin D, 20 μg/ml oligo $dT_{12-18}$ primer, 30 mM 2-mercaptoethanol, 500 units/ml reverse transcriptase (PL Biochemicals) and 100 uCi of $aP^{32}$ dCTP Incubation was carried out at 42° C. for 30 minutes. At the end of the reaction, NaOH was added to a final concentration of 0.2 N. After boiling for two minutes, the solution was neutralized with 0.2 N acetic acid, and 0.1 M Tris, pH 7.4. The mixture was applied to a G150 column and run in a buffer containing 0.3 M NaCl, 10 mM Tris 7.4, 1 mM EDTA and 0.01% SDS. The exclusion peak was pooled and the cDNA synthesized had a specific activity of about $1 \times 10^8$ cpm/μg. Duplicate sets of filters containing the cDNA clones were screened separately with $10^7$ cpm of each cDNA probe in a 10 ml hybridization buffer for 16 hours at 68° C. The signals which hybridized strongly with the cDNA prepared from poly(A) RNA at 40.5° C. and only weakly to cDNA prepared from poly(A) RNA at 35° C. were selected for further characterization.

The cDNA clone, p3C5 hybridized more intensely with {$^{32}$p} cDNA from template poly(A).RNA extracted from K12 cells incubated at 40.5° C. The size of the cDNA insert of p3C5 was determined by gel electrophptresis and estimated to be approximately 2500 nucleotides. The protein coded for by cDNA clone p3C5 was determined by hybrid-selected translation according to the method of Ricciardi et al., *Proc. Natl. Acad. Sci. U.S.A.*, 76, 4927 (1979) and found to be GRP78.

EXAMPLE I

Isolation of RAT 1 Genomic Clone

The p3C5 cDNA plasmid was used as a hybridization probe to isolate the homologous rat gene encoding for the 78-kilodalton glucose-regulated protein from a rat genomic library. The rat genomic library was obtained from Dr. T. Sargeant and the construction of the rat genomic library is described in Sargeant, T. et al., *Proc. Natl. Acad. Sci.*, 76, 3256 (1976).

The rat genome encoding for GRP78 designated RAT 1, was isolated from the rat genomic library according to the procedure described in Benton and Davis, *Science*, 196, 180-182, (1977) and Maniatis et al., *Cell*, 15, 687-701 (1978). Bacterial plates contain about 100 ml each of NZYDT plate media per liter (10g NZ amino, 5 g yeast extract, 5 g NaCl, 12.5 g agar, 10 ml of 1% diaminopimelic acid, 10 ml of 0.4% thymidine and 10 ml of 1M MgSO4).

At a titer of $7 \times 10^7$ phage/ml, 8 of the rat EcoRl genomic library was mixed with 2 ml SM (0.1M NaCl, 10 mM Tris pH 7.0, 10 mM Mgcl2, 0.1% gelatin) and 6 ml of E. coli strain KH802 grown at mid-log phase ($OD_{600}$=0.8). After incubation at 37° C. for 15 minutes, 0.28 ml of this mixture was added to 8 ml of NZYDT+Mg top agar (per liter, 10 gm NZ amine, 5 g yeast extract, 5 g NaCl, 0.7% agarose, 10 ml of 1% diaminopimelic acid, 0.4% thymidine, 1 M MgSO4) and the cultures maintained at 45°-50° C.

The phage E. coli mixture was plated on each plate. A total of 20 plates were prepared, each having about 20,000 phage in the top agar. Incubation was at 37° C. overnight. The plates were refrigerated for one hour before the nitrocellulose filters were applied. Phage and DNA were absorbed to these filters in duplicate by placing two filters on each plate sequentially, one minute for the first filter and five minutes for the second, at room temperature. The filters were then denatured for 30 seconds in 1.0 M NaCl, 0.1 M NaOH and neutralized for 30 seconds in 1.5 M NaCl, 0.5 M Tris pH 8. After blot dry on Whatmann 3mm paper, the filters were baked at 80° C. for 4-5 hours at approximately 30 mm vacuum.

The filters were hybridized with nick-translated p3C5 probe labeled to a specific activity of $5 \times 10^7$cpm/$\mu$g. To prepare the filters for hybridization to a labeled probe, they were wetted in about 10 ml filter in $3 \times$SSC ($1 \times$ =0.15 M NaCl, 0.015 M NaCitrate) at room temperature for 30 minutes, and prehybridized in "blot hybridization buffer" containing 1.0 M NaCl, 0.045 M NaCitrate, 10X Denhartdt's, 50 $\mu$g/ml poly rA, 50 $\mu$g/ml poly rC, 150 $\mu$g/ml E. coli DNA (sonicated and heat denatured). A total of $10^8$cpm of the plasmid probe was used in a hybridization reaction volume of 80 ml. Hybridization was performed at 68° C. for overnight in the same "blot hybridization buffer."

After hybridization, the filters were washed twice in agitation in 10 ml/filter of 1 M NaCl, $5 \times$Denhardt's, 0.045 M Tris, pH 8, 0.1% SDS, 0.1% Na pyrophosphate at 68° C. 30 minutes per wash; and three times in a buffer containing $1 \times$SSC, 0.1% SDS and 0.1% Na pyrophosphate. After wash, the filters were exposed to Kodak XAR5 film with a lighting plus intensifying screen for two days. The autoradiogram developed revealed five strong hybridization signals present in duplicate filters. The plaques corresponding to those signals were excised from the NZYDT plates and resuspended in 1 ml of SM medium. The titer of phage in each of the tubes was about $10^7$. Each tube was subjected to a rescreening procedure which involved plating 5000 phage from each tube into fresh NZYDT plates. The phage and DNA were bound to nitrocellulose filters as described previously and hybridized to $7 \times 10^6$cpm of nick-translated 32p labeled p3C5. The individual phage plaque which hybridized to p3C5 was picked. Five phages were isolated and DNA was prepared from each of the phage. To prepare phage DNA, each individual plaque was resuspended in 1 ml of SM medium. The phage suspension was mixed with E. coli KH802 grown up NZYDT. The mixture was allowed to incubate at 37° C. for 10 minutes. Afterwards, 2.5 ml of fresh NZYDT was added and incubation continued for overnight at 37° C. with vigorous shaking. The next day, the bacteria were lysed with addition of 2 drops of chloroform. The titer of phage obtained in the supernatant was about $1 \times 10^8$ phage/ml. Phage DNA was extracted from the lysate by the following procedure. The cell debris was pelleted by centrifugation. To the supernatant, 5 $\mu$g/ml of DNaseI and RNaseI are added. Incubation was at room temperature for 30 minutes and at 4° C. for 2 more hours. SDS was added to 0.02%, Tris to 50 mM. The mixture was extracted once with phenol and once with sevag (chloroform: isoamyl alcohol 24:1). The solution was adjusted to 0.3 M NaAc and alcohol precipitated. The DNA was resuspended in 100 lambda 10 mM Tris, pH 7, 1 mM EDTA.

The phage DNA was digested with EcoRl, and the restriction enzyme fragments generated were separated on 1% agarose gels. The fragment containing gels were blotted onto nitrocellulose filters and hybridized with about $10^7$cpm of nick-translated p3C5 DNA. The RAT 1clone contained 15 kb of rat DNA and three of its ECoRl fragments (sizes 4.3 kb, 2. 3 kb and 0.94 kb) hybridized strongly to p3C5. This rat genomic clone, as shown in FIG. 1, contained the entire sequence of the rat GRP78 genome.

The RAT 1 sequence was subjected to further restriction mapping. See Lee and Sinsheimer, *Proc. Natl. Acad. SCi., U.S. A.*, 71, 2882-2886 (1974). The restriction fragments were hybridized with $^{32}P$ labeled p3C5 to locate the sequence homologous with the hamster cDNA sequence. The region of homology is indicated in FIG. 1. To orientate the direction of transcription, 2 $\mu$g of RAT 1 DNA was digested with EcoRl, electrophoresed on 1% agarose gel and blotted onto nitrocellulose filters. The filters were hybridized with the $P^{32}$ 1.0 kb fragment derived from p3C5 restriction digested with EcoRl. This 1.0 kb fragment was shown to contain the 3' end of the cDNA since it preferentially hybridized to 3' enriched cDNA. To prepare the 3' enriched cDNA, about 5 $\mu$g of poly(A)-RNA isolated from K12 cells incubated at 40.5° C. was boiled for three minutes in 100 lambda of 50 mM Tris, pH 9.5 and cooled. The RNA was then passed over the oligo(dT) column as previously described. The poly(A)-RNA isolated this way was enriched in its 3' end. The cDNA could then be prepared as described above using the 3' enriched RNA as template. Combination of restriction mapping and hybridization with 3' cDNA defined the orientation of transcription for RAT 1 DNA as shown in FIG. 1. A 6.2 BamHI fragment was found to contain the 5' end of the rat 1 gene (FIG. 1).

EXAMPLE II

Construction of the Plasmid pUC6.2

The RAT 1 genome was digested with 50 units of BamHI in 200 lambda of reaction mixture containing 20 $\mu$g RAT 1 DNA, 150 mM NaCl, 6 mM Tris pH 7.9, 6 mM $MgCl_2$ and 100 $\mu$g/ml bovine serum albumin. Incubation was at 37° C. for four hours. The BamHI fragments were separated by electrophoresis on a 1% low melting agarose gel. The 6.2 35 kb fragment was extracted from low melting agarose gel and was suspended in 20 of 10 mM Tris, pH 7, 1 mM EDTA.

The plasmid pUC8 was digested with 32 units of BamHI in 140 lambda of reaction mixture containing 18 $\mu$g of pUC8 DNA, 150 mM NaCl. 7 mM Tris, pH 7.9, 6 mM $MgCl_2$ and 100 $\mu$g/ml bovine serum albumin. Incubation was at 37° C. for two hours. The pUC8 BamHl fragments were also separated by electrophoresis on a 1% low melting agarose gel and resuspended in 30 lambda of 10 mM Tris, pH 7, 1 mM EDTA. To eliminate vector self-religation, 4.5 µg of the BamHI cut pUC8 DNA was mixed with 1 lambda of 3M NaCl, 2.5 lambda of 0.1M Tris, pH 8, 4.5 lambda of water and 1 lambda of bacterial alkaline phosphatase (Bethesda Research Laboratory 200 units/L). Incubation was at 65° C. for 60 minutes. The mixture was extracted twice with phenol, pre-equilibrated with 1 M Tris at ph 7, and once with chloroform. The DNA in the aqueous phase was alcohol precipitated and resuspended in 15 lambda of 10 mM Tris, pH 7, 1 mM EDTA, at a final concentration of about 0.15 µg/lambda.

The 6.2 kb rat BamHI fragment was mixed with the BamHI cut pUC8 DNA and ligated in a reaction mixture containing: 10 lambda of BamHI cut 6.2 kb rat DNA (0.5 µg total), 1 lambda of BamHI cut pU8 (0.15 µg), 1.5 lambda of 10× ligation buffer 500 mM Tris pH 7.8, 100 mM MgCl$_2$, 200 mM dithiothreitol, 10 mM ATP, 500 µg/ml bovine serum albumin), 1.5 lambda of 10 mM ATP and 1 lambda of T4 DNA ligase (New England Biolabs, 100 u/lambda). Incubation was at 16° C. for 16 hours. Another 1 lambda of T4 DNA ligase was added along with 2 lambda of 10 mM ATP and incubation continued for four more hours. At that time, the resulting hybrid plasmid was transformed into the bacterial strain JM83 (C. Vieira and J. Messing, *Gene,* 19, 259 (1982)) according to the procedure of Kushner described above. Ampicillin resistant colonies were grown on ampicillin containing L broth plates.

To characterize the hybrid plasmid DNA, sample DNA was extracted from the JM83 cells and digested with 2 units of BamHI per µg DNA at 37° C. for two hours. The digested DNA was electrophoresed on 1% agarose gel. After blotting onto nitrocellulose filters, the DNA was hybridized with p3C5, nick-translated with $^{32}$PdATP to a specific activity of $2\times10^7$cpm/µg. The plasmid, designated pUC6.2, contained a 6.2 kb BamHI fragment which hybridized to p3C5.

The plasmid, pUC6.2 was further restriction mapped with a large variety of restriction enzymes. The restriction sites for these enzymes are shown in FIG. 1. One enzyme, PvuII cleaves the 6.2 kb insert DNA into four large fragments ranging in size from 2.4, 1.8, 1.1 and 0.9 kb. A small fragment of size about 100-200 nucleotides was also detected. The restriction map of the Pvu II fragments was established with double and triple enzyme digestions as previously described. Lee and Sinsheimer, *Proc. Nat. Acad. Sci. U.S.A.,* 71, 2882-2886 (1974). The order of the PvuII fragments is shown in FIG. 1.

To determine the direction of transcription, 2 µg of pUC6.2 was digested with 4 units of PvuII (New England Biolabs) in reaction mixture containing 60 mM NaCl, 6 mM Tris 7.5, 6 mM MgCl$_2$, 6 mM 2-mercaptoethanol and 100 µg/ml bovine serum albumin. Incubation was at 37° C. for three hours. The digestion mixture was applied to a 1% agarose gel and electrophoresed. The gel was stained with ethidium bromide and five bands were evident when observed under the short wave length ultraviolet light. The bands were identified as the 2.6 kb band derived from pUC8 and 4 fragments, 2.4, 1.8, 1.1 and 0.9 kb from the rat DNA insert. The DNA was blotted onto nitrocellulose filters and hybridized with $^{32}$P labeled K12 cDNA prepared from RNA extracted at 40.5° C. and cDNA prepared from glucose-starved NRK RNA. Fragments 1.8 and 1.1 hybridized to the cDNA probes, whereas the 2.4 kb did not hybridize at all. The 0.9 kb fragment faintly hybridized. This result, together with the restriction map, established the orientation of transcription as shown in FIG. 1.

DNA sequence determination of the PvuII 1.1 kb fragment further established the position of the TATA box and the CAAT sequence commonly observed in eukaryotic promoter sequences. The DNA sequence (shown in FIG. 2) of the 5' sequence of the RAT-1 gene was determined by method described by Maxam and Gilbert, Methods in Enzymology. 65. 499-561 (1980).

EXAMPLE III

Construction of the Plasmid pNE/12

Figure 3:
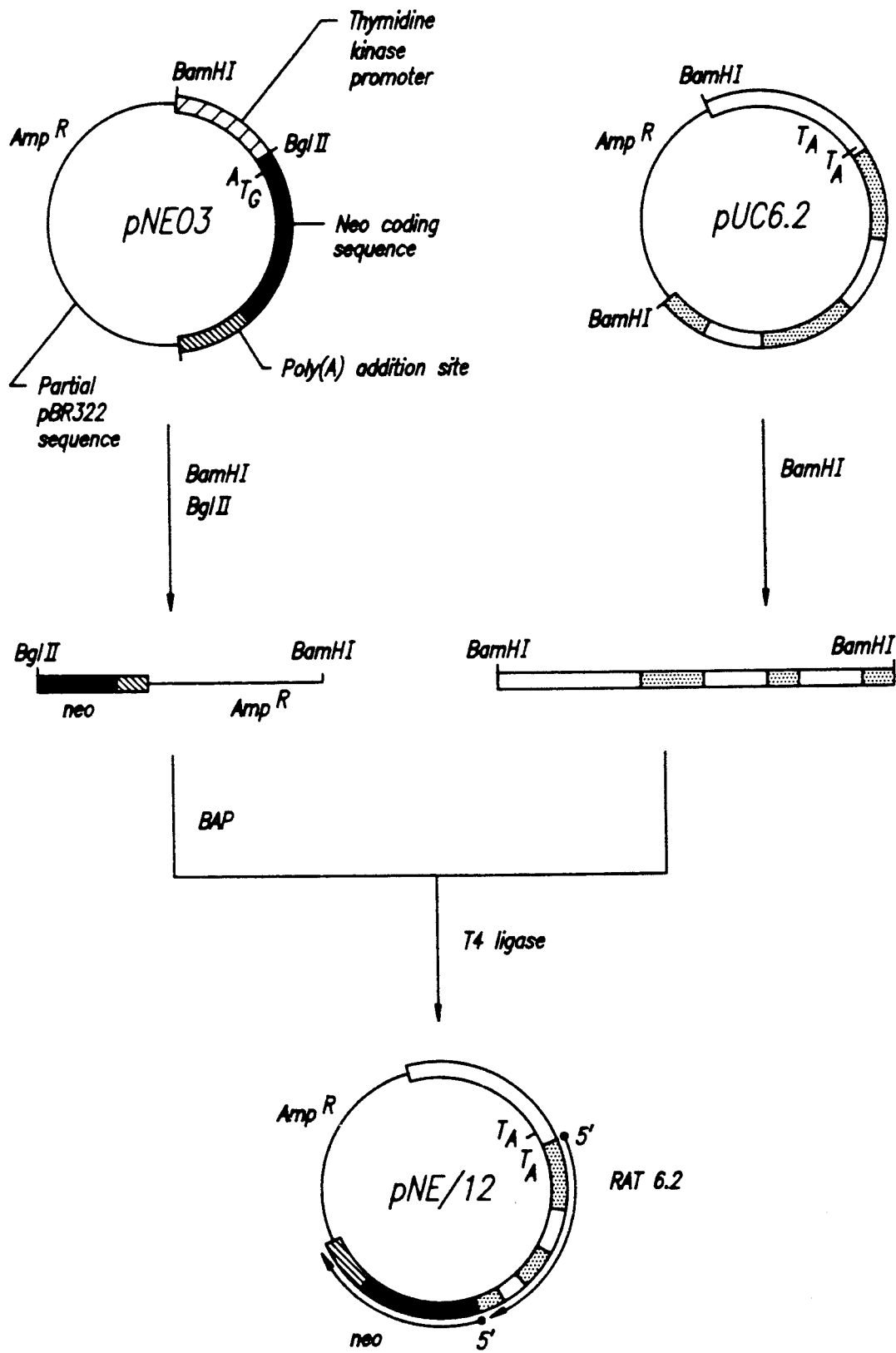
FIG. 3 shows a flow chart for the construction of the RAT 6.2 kb neo-hybrid gene of plasmid pNE/12. The relative positions of the restriction endonuclease sites used in the procedure are depicted as in FIG. 1. Amp$^R$ denotes the gene for ampicillin resistance. Neo denotes the gene for resistance to the neomycinkanamycin antibiotic G418. The orientation of the 6.2 kb BamHl fragment of RAT 1 with respect to the neo gene as depicted was determined by restriction analysis. Digestion of the plasmid pNE03 with BamHl and BglII yields a 4.4 kb fragment containing the entire neo coding sequence and partial pBR322 sequence, including the origin of replication, but no thymidine kinase promoter. Thus, the only promoter sequence present in pNE/12 is the promoter from the 6.2 kb BamHl fragment.

To determine whether the 6.2 kb BamHI fragment contained the GRP regulatory sequence a hybrid gene was constructed from the plasmid pNE03 and the 6.2 kb RAT 1 fragment. To ensure that transcription was being initiated solely by the 6.2 kb fragment the thymidine kinase promoter of pNE03 was removed. As schematically set forth in FIG. 3 the thymidine kinase promoter was removed from the pNE03 plasmid DNA by digestion in 210 lambda of reaction mixture containing 1X TA buffer, 32 units of BamHI, 16 units of BglII and 10 µg pNE03 plasmid. Incubation was at 37° C. for 1.5 hours. The digested DNA was applied to 1% low melting agarose gel. After electrophoresis the gel was stained and two bands were observed. One of the fragments was about 0.7 kb in size and contained the herpes virus thymidine kinase promoter. The fragment was about 4.4 kb and contained the neomycin resistance gene, as well as the pBR322 origin of replication. The 4.4 fragment was excised from gel and suspended in 10 mM Tris, pH 7, 1 mM EDTA.

The plasmid pUC6.2 was digested with 100 units of BamHI in 200 lambda of reaction volume containing 50 µg pUC6.2, 150 mM NaCl, 6 mM Tris pH 7.9, 6 mM MgCl$_2$ and 100 µg/ml bovine serum albumin. Incubation was for three hours at 37° C. The digested portion was applied to a 1% low melting agarose and after electrophoresis, the gel was stained. The 6.2 kb band was separated from the 2.7 kb fragment which contained the pUC8 sequence. The 6.2 kb band was excised from the gel and the DNA extracted. The DNA was resuspended in 10 mM Tris, pH 7, 1 mM EDTA at a concentration of 0.2 µg/lambda.

The rat 6.2 kb DNA was added to 4 lambda of 4.4 kb pNE03 fragment which had been treated with bacterial alkaline phosphatase and ligated in a reaction mixture containing 1.5 lambda of 10×ligation buffer, 1.5 lambda of 10 m ATP and 1 lambda of T4 DNA ligase (100 units, New England Biolabs) 4 lambda of 4.4 kb pNE03 fragment, and 1.5 µg 6.2 kb DNA. Incubation was at 16° C. hours. Another 1.5 lambda of 10 mM ATP and 1 lambda of DNA ligase were added and incubation continued for 4 hours at 16° C. This ligated mixture was transformed into *E. coli* HB101, using the Kushner procedure described above.

Stable transformants were screened for the presence of the 6.2 kb rat insert by blot-hybridizing the DNA with $7\times10^7$ cpm of nick-translated $^{32}$P labeled PvuII 1.1 kb fragment obtained from pUC6.2. The orientation of the RAT 1 6.2 kb DNA with respect to the neomycin gene was determined by restriction mapping with various restriction enzymes. Those plasmids having the 6.2 kb rat DNA in the same transcriptional orientation as the neomycin structural gene would yield fragment sizes of 5.95 kb and 4.85 kb when digested with the restriction 35 enzyme HindIII. Those plasmids in which the rat/neo hybrid gene had opposite orientations of transcription would yield fragments of 8.65 and 2.15 kb. The plasmid designated pNE/12 contained a 6.2 kb insert which hybridized with the rat PvuII 1.1 kb fragment located in the same transcriptional orientation as the neo structural gene.

EXAMPLE IV

Enhanced Transcription by High Temperature in oNE/12 Transformants

To test whether the Rat 6.2/neo hybrid gene could be induced at high levels by temperature shift to non-permissive temperatures ts K12 cells were transformed by rat 6.2/neo hybrid plasmid. Transfection was by the techniques of Parker and Stark, J. Virol., 31, 360–369 (1979). The transfecting DNA (10 μg) was mixed with 5 μg of high molecular carrier DNA (we routinely used genomic DNA extracted from Hela cells) in 190 lambda of 2×isotonic saline+HEPES buffer (0.28 M NaCl, 10 mM KCl, 1.5 mM $Na_2HPO_4$, 0.22% glucose, 40 mM HEPES). Sterile $H_2O$ was added to adjust the total volume to 380 lambda and 19 lambda of 2.5M $CaCl_2$ solution was gently bubbled into the mixture. The mixture was allowed to sit at room temperature for 30 minutes. The medium was poured away from the cells and the mixture was added to cell. Incubation was at 35° C. for 20 minutes. At that time, 10 ml of fresh DMEM was added to the cells. Incubation continued for 4 hours or overnight at 35° C. The medium was poured off and the cells were then treated with 1.5 ml of 15% glycerol in IX isotonic saline+HEPES buffer for three minutes at 35 C. Afterwards, 15 ml of fresh DMEM was added to the cells in each flask. Incubation at 35° C. was continued for two days on when the cells were about 60% confluent. At that point, G418 (neomycin) was added to the cells at a concentration of 200 μg/ml for K12 cells and 400 μg/ml for WglA cells. After about 2 weeks, resistant colonies were observed.

Four stable K12 transformants pNE/12-1, pNE/12-2, pNE/12-3, and pNE/12-4 containing the same direction of transcription for both the Rat 6.2 and neo gene were picked and expanded for analysis of neo-mRNA concentration at the non-permissive temperature of 39.5° C. Each transformant was seeded in 150 mm diameter culture dishes and grown to 90% confluency in DMEM. At this time, parallel sets of cells were subjected to control and non-permissive temperature. After 16 hours total cytoplasmic RNA was extracted from the cells. The RNA samples were applied on formamide/-formaldehyde agarose gels and after electrophoresis blotted on nitrocellulose filters.

The RNA blots were hybridized with nick-translated neo-DNA fragments (0.76, 0.72, 0.51 kb fragments) derived from PvuII digestion of pNE03. The pNE03 plasmid DNA was purified by the CsCl-EtBr banding and was digested with 40 units of BamHI and 40 units of PvuII in lX TA buffer in a total volume of 100 lambda. Incubation was at 37.C for three hours. The digested DNA was applied onto a 1% low melting agarose. After electrophoresis, the gel was stained. Three fragments, sizes 0.76, 0.72 and 0.51 kb were excised from the gel. These fragments contained the neomycin resistance gene. DNA was extracted from the low melting gel, alcohol precipitated and resuspended in 10 mM Tris, pH 7, 1 mM EDTA. The DNA was purified by passage over an elute-trip (Schneider and Schnell) and alcohol precipitated. The DNA was resuspended in 10 mM Tris, pH 7, 1 mM EDTA. For the preparation of the $^{32}P$ probe, about 2 μg of the pooled PvuII fragment was used in each nick-translation reaction mixture. The specific activity of the probe averaged around $2\times10^8$cpm/μg. The specific activity of the neo probes ranged from $2-4\times10^8$ cpm/μg DNA.

Figure 4:
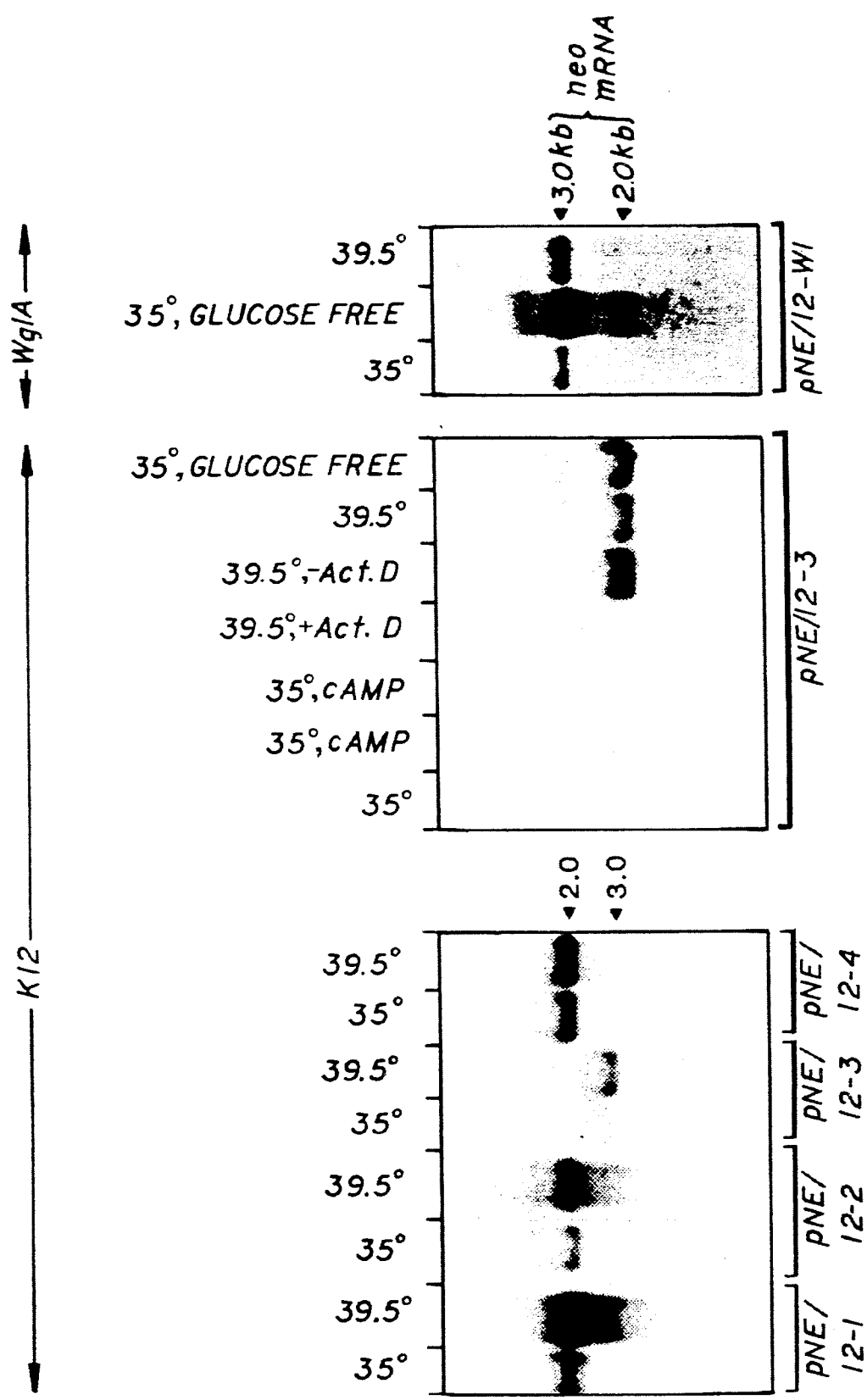
FIG. 4 is an autoradiogram showing the level of neo-mRNA in stable pNE/12 transformants of Chinese hamster cell lines K12 and WglA under conditions of glucose starvation or high temperature. The results were obtained by RNA blot-hybridization with nick-translated neo-DNA fragments.

Examples of the RNA blot hybridization results are shown in FIG. 4A. In each case the magnitude of neo transcripts was enhanced 5-10 fold by high temperature.

EXAMPLE V

Enhanced Transcription by Glucose Starvation in pNE/12 Transformants

In order to determine whether the RAT 6.2/neo hybrid gene could be enhanced by glucose starvation the K-12 transformant pNE/12-3 was picked and expanded according to the procedure of Example IV. After the culture dishes had reached 90% confluency parallel sets of cells were subjected to conrol and different culture conditions as follows: 35° C. in DMEM; 35° C. in DMEM supplemented with 0.5 mM dibutyl-cAMP, 1.0 mM theophylline; 35° C. in DMEM supplemented with 0.2 μM dexamethasone in addition to dibutyl-cAMP and theophylline; four hours at 39.5° C in DMEM with Actinomycin D after the cells were treated with 4.5 μg/ml Actinomycin D for two hours at 35° C.; four hours at 39.5° C. in DMEM; 16 hours at 39.5° C. in DMEM; and 16 hours at 35° C. in glucose-free medium.

The RNA blot hybridization results are shown in FIG. 4B. As in the case of the p3C5 transcripts, the neo transcripts were specifically induced by glucose starvation. Actinomycin D, an inhibitor of transcription, eliminated the response.

EXAMPLE VI

Enhanced Transcription by Glucose Starvation in WglA Transformants

To test whether the GRP regulatory sequence of the hybrid rat 6.2/neo gene can induce transcription in non-mutant WglA fibroblast cells the stable transformant pNE/12-Wl derived from transfecting WglA with pNE/12 was picked and expanded according to the procedure of Example IV. After the culture dishes had reached 90% confluency in DMEM the parallel sets of cells were subjected to control and different culture conditions as follows: 35° C. in DMEM; 16 hours at 35°. C. in glucose-free medium; and 17 hours at 39.5° C. in DMEM. Of the five transformants tested which contained pNE/12, three transformants demonstrated a three to sixfold increase in neo-mRNA under glucose starvation conditions. In contrast to the K12 transformants, the WglA transformants showed only a 1.5 to 2 fold increase in neo-mRNA levels when shifted to 39.5° C. The RNA blot hybridization of pNE/12-Wl is shown in FIG. 4C. This observation was directly parallel to our previous observation that in WglA, the p3C5 mRNA was regulated by glucose starvation at 35° C. but was only slightly affected by increasing the temperature.

EXAMPLE VII

Enhanced Transcription by Calcium Shock in WglA Transformants

Figure 5:
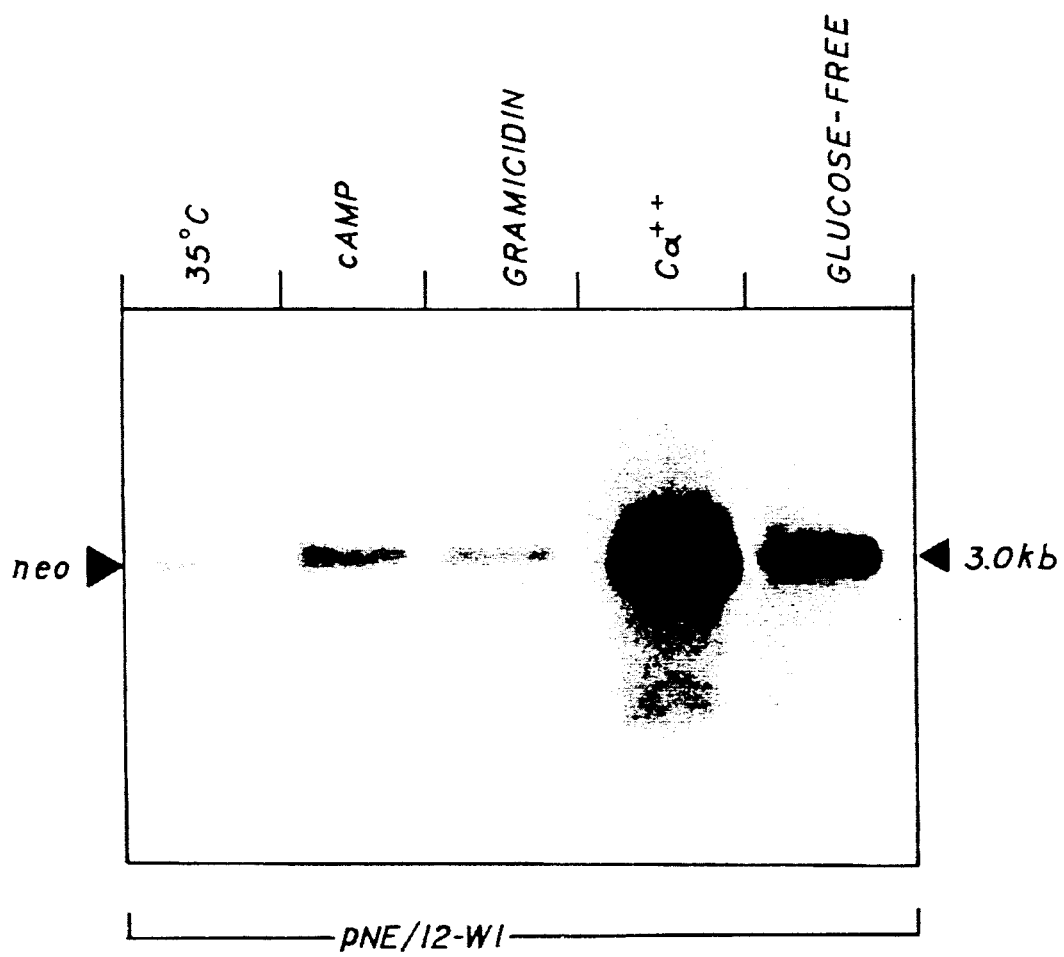
FIG. 5 is an autoradiogram showing the increased level of neomRNA transcribed by stable pNE/12 transformants of WglA cells under conditions of calcium shock and glucose starvation.
Figure 6:
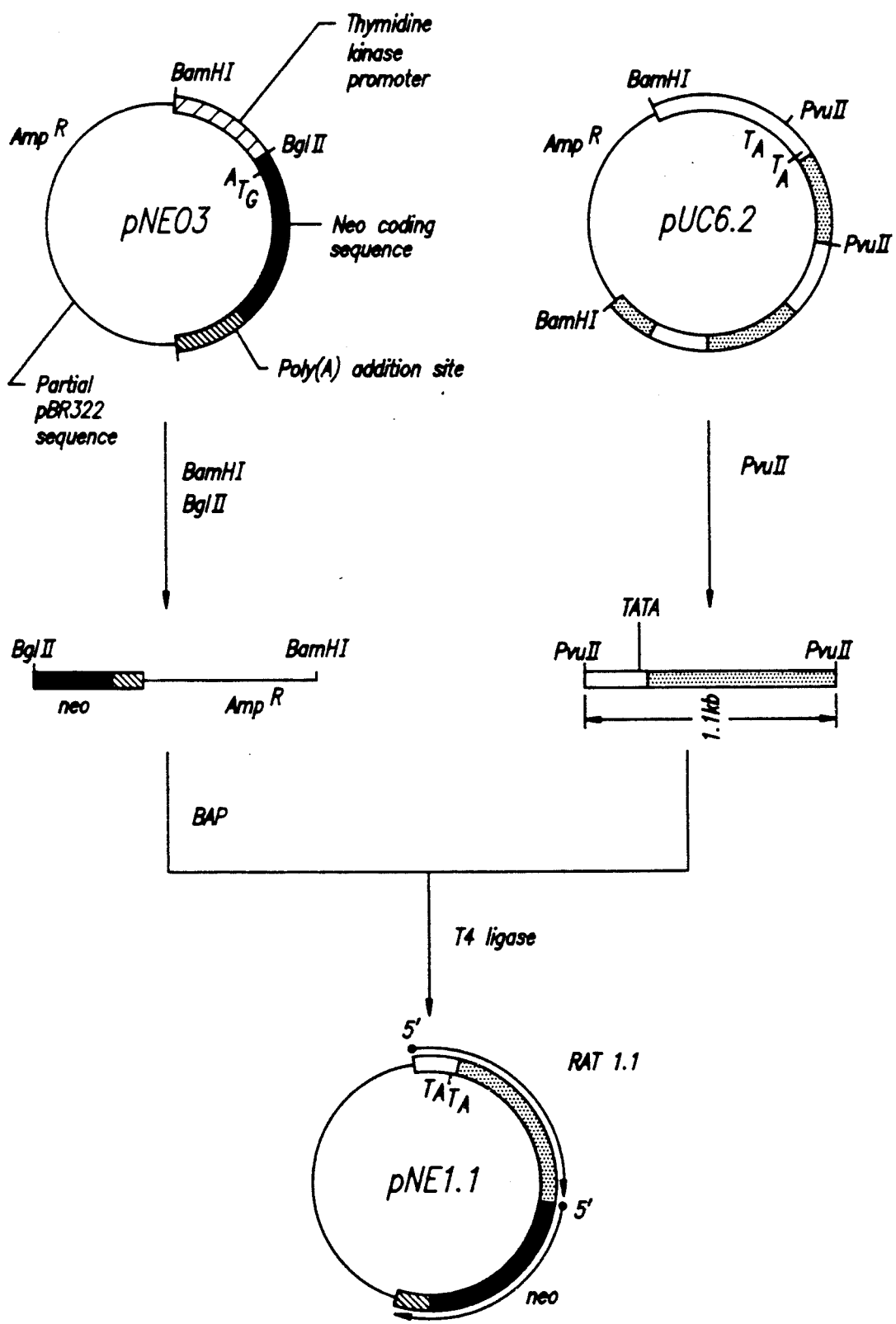
FIG. 6 shows a flow chart for the construction of the RAT 1.1 neo hybrid gene of plasmid pNE/1.1. The relative positions of the endonuclease sites used in the procedure along with the Amp$^R$, neo gene, and restriction sites flanking the thymidine kinase promoter are depicted as in FIG. 3.

To test whether the GRP regulatory sequence of the hybrid rat 6.2/neo hybrid gene could induce transcription by calcium shock the transformant pNE/12-W1 was picked and expanded according to the procedure of Example VI. The cells were incubated either in complete DMEM, in DMEM supplemented with 0.1 mM dibutyryl cAMP, in DMEM supplemented with 1 $\mu$M gramicidin (a monovalent cation inophore), DMEM supplemented with 7 $\mu$M calcium inophore A23187, and glucose-free DMEM. Treatment was for 16 hours at 35° C. The RNA blot hybridization results are shown in FIG. 5. As expected, the level of 6.2/neo hybrid mRNA was elevated 15-fold by A23187 treatment and 15-fold by glucose starvation, but was relatively unaffected by dibutyryl cAMP or gramicidin.

EXAMPLE VIII

Construction of Plasmid pNE 1.1

Figure 7:
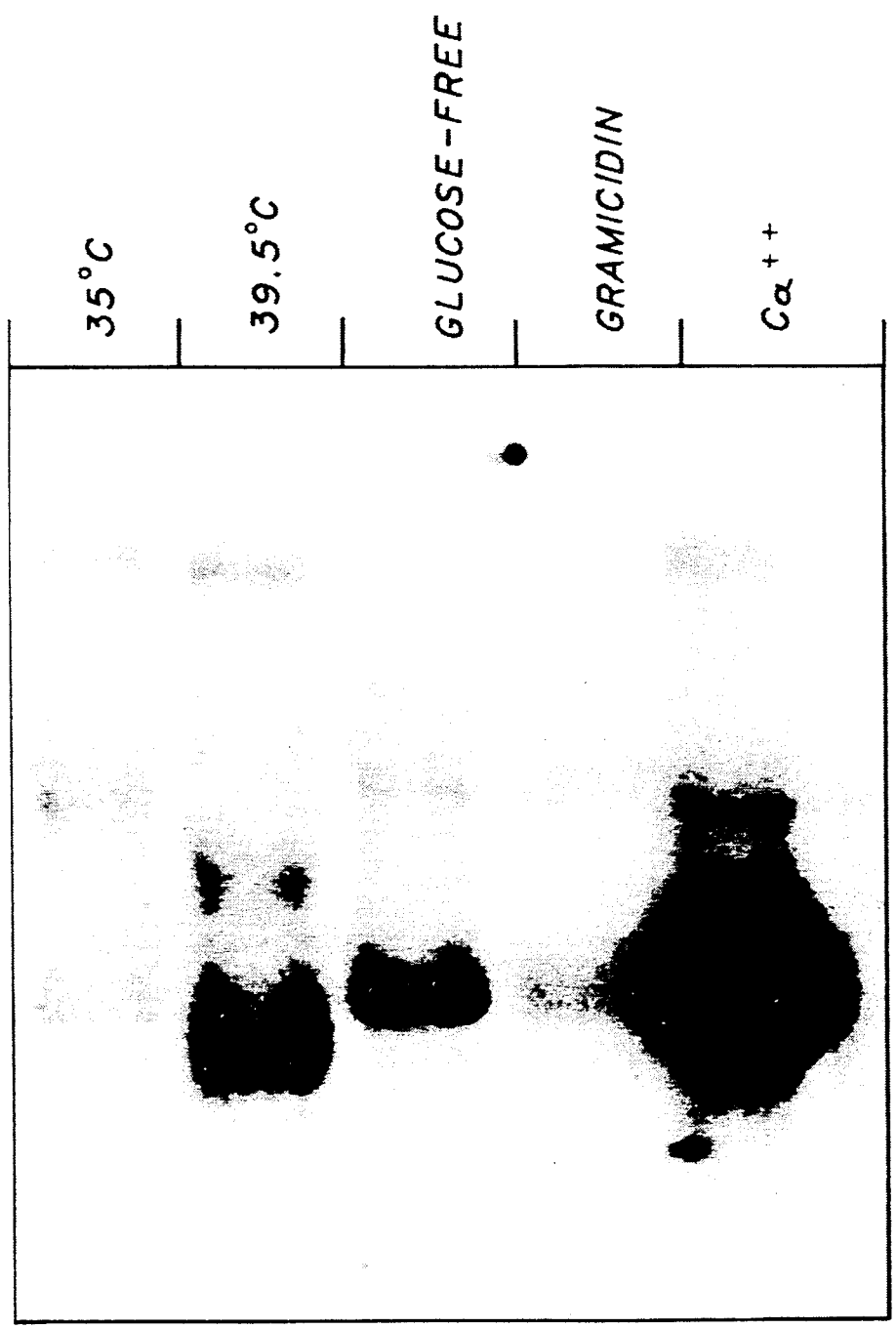
FIG. 7 is an autoradiogram showing the level of neo-mRNA transcribed by stable pNE/1.1 transformants of the K12 cell line under conditions of glucose starvation, calcium shock and high temperature.

To further identify the region of the RAT 1 gene containing the GRP regulatory sequence the 1.1 kb PvuII fragment of pUC6.2 was inserted into pNE03 without the Herpes thymidine kinase promoter to form a rat/neo hybrid gene (FIG. 7). The plasmic pNE03 was digested with 30 units of BamHI and 30 units of BglII in a total volume of 150 lambda containing 1×TA buffer (66 mM KAc, 10 mM MgCl$_2$, 33 mM Tris, pH 7.4 and 0.5 mM DTT) and 15 $\mu$g pNE03. After 1.5 hours at 37° C., the volume was adjusted to 300 lambda by addition of 10 mM Tris, pH 7, 1 mM EDTA and the reaction was extracted twice with pre-equilibrated phenol (pH 7) and once with chloroform. The solution was adjusted to 0.3 M NaAc, pH 5.4 and alcohol precipitated. After the DNA was resuspended in 15 lambda of 10 mM Tris, pH 7.4, 2.5 lambda of 0.1 M Tris, pH 8, 1 lambda of 3 M NaCl, 5.5 lambda of H$_2$O and 2 lambda of bacterial alkaline phosphatase (200 units/ lambda) were added. Incubation was carried out at 65° C. for 60 minutes. After the addition of 150 lambda of gel electrophoresis buffer, the samples were applied into 1% low melting agarose. The 4.4 kb fragment from pNE03 was isolated and purified by passage through elute tip column, and alcohol precipitated.

The 4.4 kb pNE03 DNA fragment was treated with the Klenow fragment of DNA polymerase to fill in the 5' protruding ends of the BamHI and BglII restriction sites. In a 50 lambda reaction volume containing 3 $\mu$g of the 4.4 kb fragment, 5 lambda of 10X nicktranslation buffer (500 mM Tris, pH 7.8, 50 mM MgCl$_2$ and 500 $\mu$g/ml bovine serum albumin), 2.5 lambda each of dATP (500 $\mu$M stock), dCTP Bochringer Manheim, 5 units/lambda, Murray, N. E. and Kelley, W. S., *Molec. Gen. Genet.*, 175, 77 (1979). Incubation was at 37° C. for 30 minutes. The solution was phenol extracted once, chloroform extracted once and the aqueous phase was alcohol precipitated. The now blunt ended 4.4 kb pNE03 DNA fragment was resuspended in 10 mM Tris, pH 7, 1 mM EDTA and ready to be ligated with the PvuII 1.1 kb fragment.

The PvuII 1.1 kb fragment was prepared by digesting 100 $\mu$g of pUC6.2 DNA with 200 units of PvuII in 60 mM NaCl, 6 mM Tris, 7.5, 6 mM MgCl$_2$, 6 mM 2-mercaptoethanol, and 100 $\mu$g/ml bovine serum albumin. The incubation was at 37° C. for four hours. The digested DNA was applied to 1% low melting agarose gels and after electrophoresis, the 1.1 kb band was excised. The DNA was extracted from the low melting agarose gel, passed over the elute tip column and alcohol precipitated.

For the ligation of the PvuII 1.1 kb fragment with the 4.4 pNE03, 0.33 $\mu$g of the PvuII fragment was mixed with 0.5 $\mu$g of pNE03 DNA in 3 lambda of 10X ligation buffer, 2.1 lambda of 10 mM ATP, 3 lambda of 0.25 M Tris, pH 8, and 4 lambda of T4 DNA ligase (500 units) were added. The final volume was adjusted to 30 lambda with water. The mixture was incubated at 22° C. for 16 hours. 2 lambda of 10 mM ATP and another 2 lambda of T4 DNA ligase were added. After four hours at room temperature, the DNA was used to transfect HB101 cells using the Knushner procedure previously described. A total of 300 ampicillin resistant colonies were obtained 12 of which were picked for preparation of plasmid DNA. One recombinant, pNE/1.1 contained the PvuII 1.1 kb fragment fused to the pNE03 without the original thymidine kinase promoter. The orientation of transcription of the rat sequence with respect to the neomycin resistance gene was determined by digestion of the hybrid plasmid with EcoRl and StuI. The plasmid which generated a 5 kb and 0.56 kb fragment contained the right orientation as shown in FIG. 7.

EXAMPLE IX

Enchanced Transcription by pNE/1.1 Transformants

To test whether the plasmid pNE/1.1 contained within its 1.1 kb rat DNA insert the GRP regulatory sequence K12 cells were transformed and expanded according to the procedure of Example IV. After culture dishes had reached 90% confluency in DMEM parallel sets of cells were subjected to control and different culture conditions as follows: 35° C. in DMEM; 17 hours at 39.5° C. in DMEM; 16 hours at 35° C. in glucose-free DMEM; 16 hours at 35° C. in DMEM supplemented with 1 $\mu$M Gramicidin; and 16 at 35° C. in DMEM supplemented with 7 $\mu$M calcium inophore A23187. The neo-mRNA was extracted and blot hybridized with neo-mRNA probe as described in Example I. The autoradiogram showing the blot hybridization results is set forth in FIG. 8. The results show the rat/neo hybrid gene transcription levels were induced to high levels under conditions of glucose starvation, calcium shock, and high temperature. Accordingly, the entire GRP regulatory sequence is located within the 1.1 kb PvuII fragment.

EXAMPLE X

Construction of Plasmids pNESS19 and pNESS41

To further define the region within the RAT 1 genome containing the GRP regulatory sequence pUC6.2 was digested with 120 units of SmaI and 120 units of StuI (New England Biolabs) (FIG. 9). The total reaction volume of 500 lambda contained 61 $\mu$g pUC6.2, 20 mM KCl, 6 mM Tris, pH 8, 6 mM MgCl$_2$, 6 mM 2-mercaptoethanol and 100 $\mu$g/ml bovine serum albumin. After incubation at 37° C. for 3 hours, the DNA was applied into a 2% low melting agarose gel. The 292 nucleotide SmaI/StuI fragment was excised and DNA extracted from the low melting agarose. After purification on an elute trip column, the DNA was resuspended in at a concentration of 1.85 $\mu$g per 20 lambda of 10 mM Tris, pH 8, 1 mM EDTA.

BamHI linker d(CGGATCCG) was purchased from New England Biolabs. The BamHI linker was dissolved in 20 lambda of H$_2$O in a final concentration of 2.5 μg/lambda. To 6 lambda of this DNA, 3 lambda of 10X linker kinase buffer (0.66 mM Tris, pH 7.6, 10 mM ATP, 10 mM Spermidine, 0.1 M MgCl$_2$, 150 mM DTT, 2 mg/ml bovine serum albumin), 16 lambda H$_2$ O and 5 lambda of T4 DNA ligase (Boechringer Manheim, 11 units/lambda) was added to a final volume of 30 lambda. Incubation was at 37° C. for 1 hour.

At the end of the reaction, 30 lambda of the BamHI linker was added to 15 lambda of 292 kb Sma/Stu fragment (1.2 μg) along with 2 lambda of 10× linker dinase buffer, 1200 units of T4 DNA ligase (New England Biolabs) were added to a total volume of 50 lambda. Incubation was at 22° C. for 16 hours. To stop the reaction 2.5 lambda of 0.5 M EDTA was added. After adjusting the volume to 250 lambda by the addition of 200 lambda of 0.3 M NaAC, pH 5.4, the solution was extracted once with sevag (phenol: isoamyl alcohol 24:1), once with chloroform and alcohol precipitated. The DNA was pelleted by centrifugation and resuspended in 40 of 10 mM Tris, pH 8, 1 mM EDTA.

The 0.292 Sma/StuI DNA linked to BamHI linker was then digested with BamHI. The above DNA in 40 lambda EDTA was added to 8 lambda of 10×BamHI buffer (1.5 M of NaCl, 60 mM Tris, pH 7.9, 60 mM MgCl$_2$, 1 mg/ml bovine serum albumin), 120 units of BamHI and 20 lambda H$_2$O. The total volume is 80 lambda. After incubation at 37° C. for three hours, the DNA was applied onto a 2% low melting agarose gel to separate the 0.292 kb fragment from the cut BamHI linkers.

For the preparation of the 0.292 SmaI/StuI plasmid, 40 μg of pNE03 DNA was digested with 130 units of BamHI in 400 lambda of reaction mixture containing 80 lambda of 5× BamHI buffer. After incubation at 37° C. for three hours, the DNA was extracted twice with sevag and once with chloroform and 40 lambda of 3 M NaAc pH 5.4 was added. The DNA was alcohol precipitated. After centrifugation to pellet the DNA, the BamHI cut pNE03 was resuspended in 45 lambda of 10 mM Tris, pH 7, 1 mM EDTA.

The 0.292 kb SmaI/StuII fragment was ligated with pNE03, in a reaction mixture containing the 0.292 kb SmaI/StuI fragment, 200 ng of BamHI cut pNE03 in a total volume of 7 lambda of 10 mM Tris, pH 7, 1 mM EDTA. To this, 1 lambda of 10× ligation buffer, 400 units of T4 DNA ligase, 1 lambda of 10 mM ATP was added to a total volume of 10 lambda. The mixture was incubated at 22° C. for 16 hours. After the incubation period, the DNA was transformed into HB101 by the Knushner procedure as previously described.

About 100 transformants were obtained as ampicillin resistance colonies. The transformants were individually picked and plated onto a fresh ampicillin plate. The colonies were transferred to nitrocellulose filters and screened by cDNA colony hybridization. The probe used is $^{32}$P labeled PvuII 1.1 kb fragments. Colonies hybridizing this probe contained the 0.292 SmaI/StuI fragment. The orientation of the 0.292 fragment with respect to the neo resistance gene was determined by digestion of the plasmid with BsshII and BglII. As indicated in FIG. 9, the plasmid with the same orientation (pNESS41) yielded a 900 nt band and the one with the opposite orientation (pNESS17) yielded a band of 656 nt.

EXAMPLE XI

Enhanced Transcription by pNESS41 and pNESS17 Transformants

To test whether the 0.292 kb SmaI/StuI fragment contained the GRP regulatory sequence K12 cells were transformed and expanded as described in Example IV. Two such transformants pNESS17 and pNESS41 were selected. After the cells reached 90% confluency, they were subjected to different culture conditions as follows: 16 hours at 35° C. in glucose-free DMEM: 16 hours at 39.5° C. in DMEM; 16 hours at 35° C. in DMEM supplemented with 1 μM Gramicidin; 16 hours at 35 C. in DMEM supplemented with 7 μM A23187; and 35° C. in DMEM.

Figure 10:
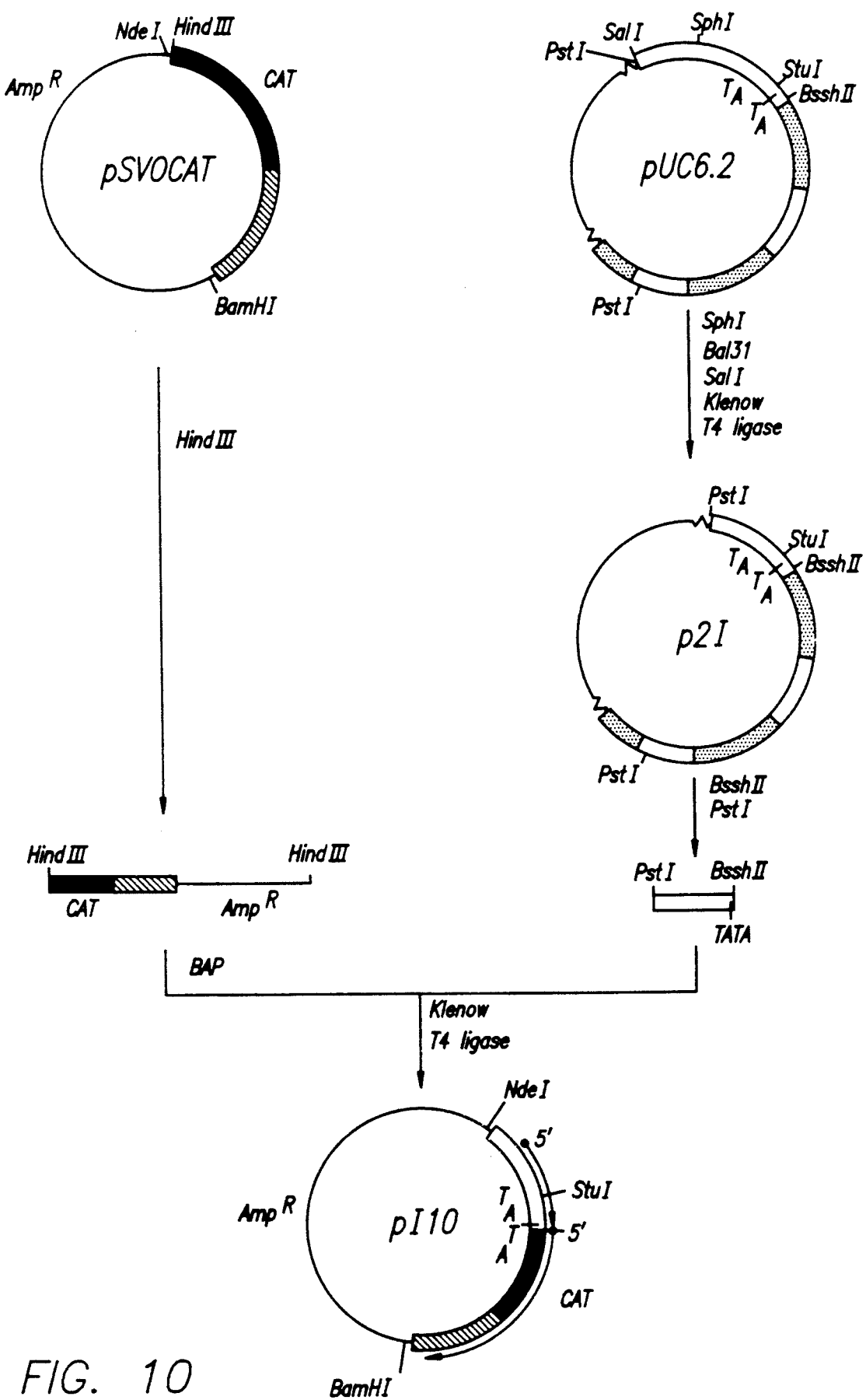
FIG. 10 shows a flow chart for the construction of plasmid pI10. In this procedure the parent plasmid pSVOCAT was used. CAT designates the chloramphenicol acetyl transferase gene.
Figure 11:
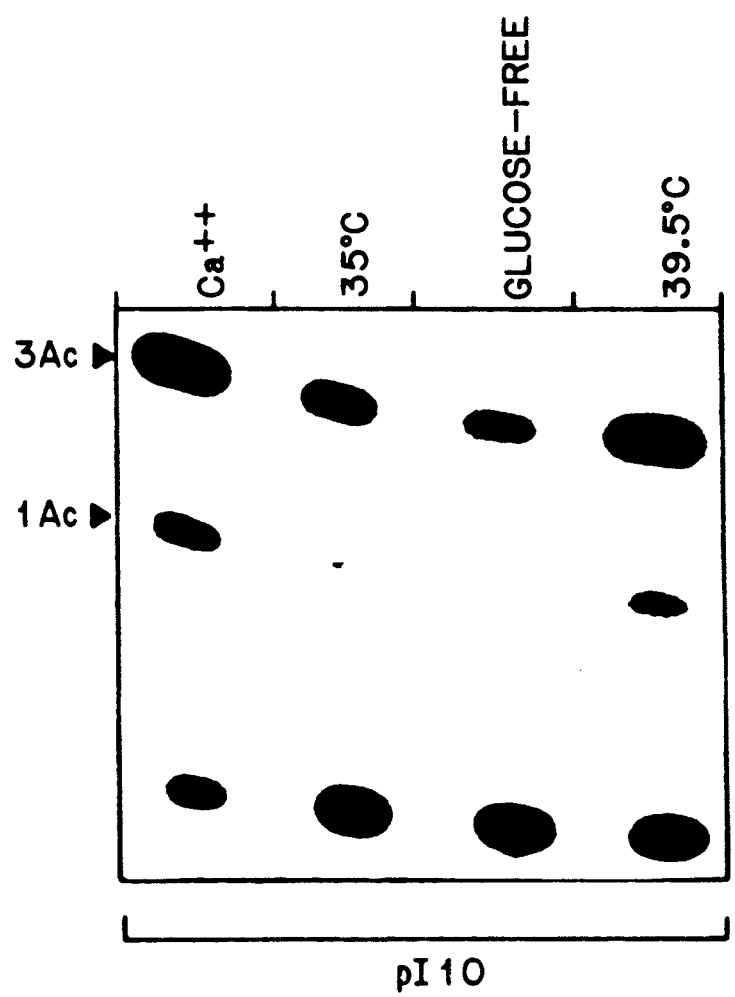
FIG. 11 is an autoradiogram showing CAT activity in the K12 cell transformed by pI10 under conditions of glucose starvation, calcium shock, or high temperature.

The results of the blot-hybridizations are shown in FIG. 10. As shown, the 0.292 SmaI/StuI fragment can enhance neo transcription under conditions of glucose starvation and calcium shock regardless of its orientation with respect to the neo structural gene. The general basal level of neo expression at 35° C in regular DMEM was also enhanced greatly, as compared to pNE03 alone which only contains the Herpes thymidine kinase promoter. The 0.292 SmaI/StuI fragment, however, was unable to enhance neo transcription by high temperature suggesting that the region of the GRP regulatory sequence responsible for temperature control exists within the StuI/BsshII fragment at the 3' end of the regulatory sequence.

Further, the neo transcriptional levels were higher in the pNESS17 and pNESS41 cultures than the pNE03 culture. Since all three plasmids contain the thymidine kinase promoter the results demonstrate the ability of the 0.292 SmaI/StuI fragment to enhance the transcription of non-GRP promoter sequences. Thus, the GRP regulatory sequence can be used to form hybrid regulatory sequences having non-GRP promoters and still be capable of enhancing transcription under conditions of glucose starvation or calcium shock.

EXAMPLE XII

Construction of Plasmid pI10

To further define the regulatory sequences in the GRP regulatory sequence, we used the fast transient transfection assay, developed by C. M. Gorman et al., *Mol Cell Bio*, 2, 1044–1051 (1982). In these assays, the GRP regulatory sequence was ligated 5' upstream to a bacterial gene encoding for chloramphenicol acetyl transferase (CAT). After transfection into culture cells, the hybrid plasmid will migrate to the nucleus and within 48–72 hours, active CAT will be synthesized. By preparing cell extracts under various induction conditions, the activity of the promoter can be determined. In addition, if various promoters are ligated 5' to the CAT gene and transfected into the same cells, the relative strengths of various promoters can be compared based on the CAT activity. This assay tests the strengths of regulatory sequences when the exogenous DNA is not integrated into the host chromosome, therefore eliminating the variability sometimes observed in stable transformants due to insertion into various chromosomal locations. The plasmid constructed for this assay was designated pI10.

The construction of pI10 is schematically set forth in FIG. 10. About 15 μg of pUC6.2 was digested with 30 units of SphI in 100 lambda of reaction mixture containing 150 mM NaCl, 6 mM Tris, pH 7.4, 6 mM MgCl$_2$, 10 mM 2-mercaptoethanol, 100 μg/ml bovine serum albumin. Incubation was at 37° C. for three hours. The mixture was extracted once with sevag, once with chloroform and alcohol precipitated.

The SphI treated DNA was resuspended in 200 lambda of 10 mM Tris, pH 7, 1 mM EDTA and 40 lambda of the DNA was digested with nuclease Bal-31. The DNA was adjusted to 600 mM NaCl, 12 mM CaCl$_2$, 20 mM Tris, pH 8, 1 mM EDTA, 8 lambda of nuclease Bal 31 (New England Biolabs, diluted to 0.2 units/lambda) were added for two minutes at 30° C. The reaction was stopped by addition of equal volume of sevag, the aqueous phase was extracted once with chloroform and the DNA alcohol precipitated. About 1.3 kb of the rat sequence upstream of the BsshII site remained after the Bal 31 digestion.

The DNA was resuspended in 50 lambda of 10 mM Tris, pH 7.4, 1 mM EDTA and was digested with 20 units of SalI in 150 mM NaCl, Tris, pH 7.9, 6 mM MgCl$_2$, 6 mM 2-mercaptoethanol and 100 μg/ml bovine serum albumin at 37° C. for two hours. The mixture was extracted once with sevag, chloroform and alcohol precipitated after centrifugation.

The SalI DNA fragment was resuspended in 32 lambda of 10 mM Tris, pH 7.4, 1 mM EDTA. About 27 lambda of the SalI DNA was added to 5 lambda of 10X nick-translation buffer (500 mM Tris, pH 7.8, 50 mM MgCl$_2$ and 500 μg/ml bovine serum albumin), 2.5 lambda each of 50 μM dATP, dCTP, dGTP and dTTP and 2 lambda of Klenow fragment of DNA polymerase 1 (Boehringer Mannheim, 5 units/lambda) were added. The final volume was adjusted to 50 lambda with H$_2$O. After 37° C. for 30 minutes, the mixture was heated at 70° C. for 5 minutes, extracted 30 once with sevag, once with chloroform and alcohol precipitated. The DNA was recovered by centrifugation and resuspended in 14.6 lambda of 10 mM Tris, pH 7, 1 mM EDTA, and 2 lambda of 10X ligation buffer (500 mM Tris, pH 7.8, 100 mM MgCl$_2$, 200 mM DTT and 500 μg/ml bovine serum albumin), 1.4 lambda 10 mM ATP and 2 lambda of T4 DNA ligase (200 units/lambda) was added. Incubation at room temperature continued for four hours.

The ligated DNA was transformed into HB101 by the Knushner method as previously described. About 500 ampicillin resistant colonies were recovered. Small scale plasmid DNA were isolated from 24 of these colonies. One clone, designated p2I, yielded a plasmid which when digested with BsshII and PstI yielded three fragments of size 3.4, 2.8 and 1.3 kb. The 1.3 kb fragment contained the GRP regulatory sequence.

About 5 μg of 1.3 kb BsshII/PstI fragment was purified from a 1% low melting agarose gel. After elute-tip treatment, the 5' ends of this fragment were filled in Klenow fragment of DNA polymerase I as previously described. Essentially, 32 lambda of this DNA was mixed with 5 lambda of 10X nick-translation buffer, and 7.5 lambda each of 50 μM of dATP, dCTP, dGTP and dTTP, and 2 lambda or 10 units of the Klenow fragment were added. The final volume was 50 lambda. After 37° C. at 30 minutes, the DNA was extracted once with sevag, once with chloroform and alcohol precipitated. The DNA was resuspended in 10 mM Tris, pH 7, 1 mM EDTA.

About 20 μg of pSVOCAT was digested with 40 units of HindIII in 66 mM KAc, 10 mM MgCl$_2$, 33 mM Tris, pH 7.8 and 0.5 mM DTT at 37° C. for two minutes. The DNA was sevag extracted, chloroform extracted and alcohol precipitated. To prevent self-ligation of the vector, the Hind III cut pSVOCAT DNA was resuspended in 15 lambda of 10 mM Tris, pH 7, 1 mM EDTA, 1 lambda of 3 M NaCl, 2.5 lambda of 0.1 M Tris, pH 8, 5.5 of Hz0 and 2 lambda of bacterial alkaline phosphatase (200 units/lambda). After 60 minutes at 65° C., the reaction mixture was extracted once with phenol, once with chloroform and alcohol precipitated. The DNA was resuspended in 20 lambda of 10 mM Tris, pH 7, 1 mM EDTA and the 5' protruding ends of the HindIII ends were filled in with the Klenow fragment of DNA polymerase I as described above.

The HindIII cut pSVOCAT was ligated with 0.148 μg of the 1.3kbk BsshII/PstI fragment in a 20 lambda reaction volume containing 0.25 μg HindIII cut pSVO-CAT, 2 lambda of 10X ligation buffer (500 mM Tris, pH 7.8, 100 mM MgCl$_2$, 200 mM DTT, 500 μg/ml BSA), 1.4 lambda of 10 mM ATP and 400 units of T4 DNA ligase. After an overnight incubation at 22° C. 1.4 lambda of 10 mM ATP and 400 units of T4 DNA ligase were added. The mixture was transformed into HB101 cells by the procedure of Knushner as previously described. About 350 ampicillin resistant colonies were obtained. The plasmid pI10, hybridized strongly with the $^{32}$P labeled PvuII 1.1 kb fragment derived from PvuII digestion of pUC 6.2.

The orientation of 1.3 kb BsshII/PstI fragment with respect to the CAT structural gene was tested by restriction digestion of pI10 plasmid DNA. For example, when this plasmid was cleaved with AvaI and BamHI, two fragments were generated, their sizes were 3.65 and 1.95 kb. Similar results were obtained with SmaI and BamHI digestion. Upon digestion with PvuII and BamHI, two fragments, 3.9 and 1.50 kb were obtained. Those results indicated that the 1.3 kb BsshII/PstI fragment was ligated in the same transcriptional orientation as the CAT gene. The structure of pI10 is shown in FIG. 10.

EXAMPLE XIII

Enhanced CAT Expression by pI10 Transformants

To determine whether the plasmid pI10 contained the region of the GRP regulatory sequence which enhances transcription by high temperature, calcium shock and glucose-starvation K12 cells were transfected by the method as described in Example IV. After transfection, parallel sets of cells were subjected to different culture conditions as follows: 16 hours at 35. in DMEM containing 7 μM A23187; 35° C. in DMEM; 16 hours at 35° C. in glucose free DMEM; 16 hours at 39.5° C. in DMEM.

The level of CAT activity was determined according to the procedure of C. M. Gorman, et al., id. Basically, cells were washed with 3X PBS (without Ca/Mg). The cells were suspended in 1 ml Tris-EDTA-NaCl (0.04 M Tris HCl, ph 7.4, 1 mM EDTA, 0.15 M NaCl), and allowed to set at room temperature for five minutes. The cells were disrupted by freeze-thaw three times. The cell debris was spun down in a microfuge and the supernatant assayed for CAT activity. In a final volume of 150 μl, 5μl $^{14}$C chloramphenicol (40–50 mCi/m-mole), 35 μl H$_2$O, 70 μl 1M Tris HCl (ph 7.8), 20 μl 4 mM acetyl CoA and 20 μl supernantant were combined. Incubation was for 30 minutes at 37° C. The chloramphenicol was extracted with 1 ml ethyl acetate for 30 seconds and centrifuged. The ethyl acetate phase was dried and 30 μl were spotted on silica gel TLC. The TLC was developed in chloroform/methanol (95/5) and exposed against XAR-2 Kodak film.

Figure 12:
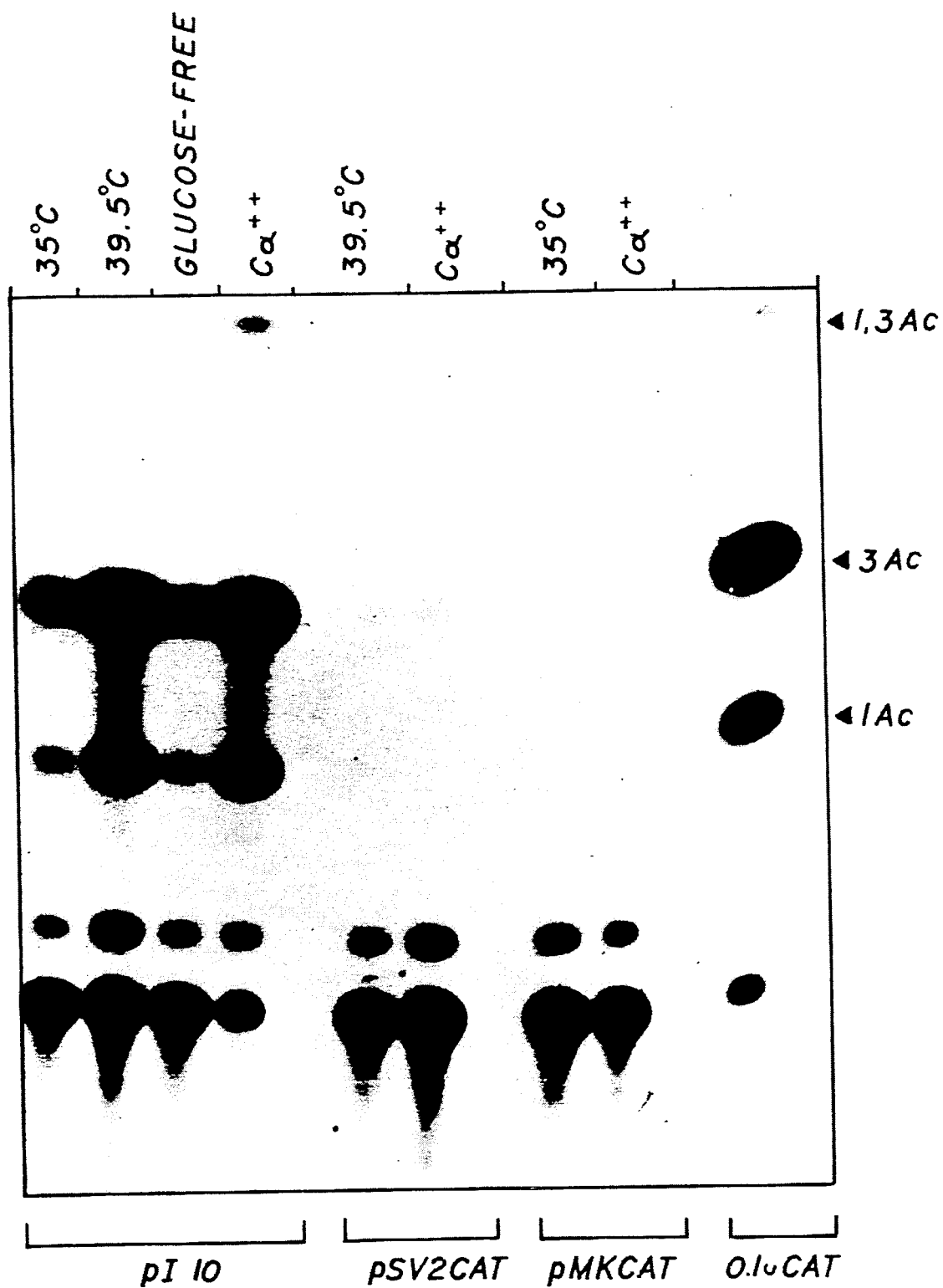
FIG. 12 is an autoradiogram showing CAT activity in K12 cells transformed by pI10, pSV2CAT and pMKCAT under various conditions.

The results of the CAT assay are shown in FIG. 12. The results show that pI10 can enhance CAT synthesis by high temperature in K12 cells. This demonstrates that the region of the GRP regulatory sequence for enhancement of transcription by high temperature lies within the StuI/BsshII restriction sites at the 3' end of the regulatory sequence. Further, as expected pI10 can also enhance CAT under conditions of calcium shock. The CAT activity obtained under glucose starvation condition was about the same as the normal medium control. However, during glucose starvation, the cells arrested their protein synthesis, and less protein was therefore added to the assay. The failure to induce under glucose starvation conditions may be due to the difference in the protein added. Another possible explanation is that for pI10 to enhance transcription by glucose starvation, the plasmid must be incorporated into the nucleus of the cell which does not occur in the CAT assay.

Further deletion of the 5' regulatory sequence demonstrates that about 500 nucleotides upstream of BsshII site contain sufficient information for induction by A23187 or high temperature in K12 cells.

EXAMPLE XIV

Relative Strengths of GRP Regulatory Sequence in Comparison to the SV40 or Metallothionein Promoters in Hamster Cells To determine the relative strength of the GRP regulatory sequence we compared the transcription levels of the GRP regulatory sequence with those of the SV40 and metallothionein promoters. Both the SV40 and metallothionein promoters are commonly used. The SV40 is constitutively expressed whereas the metallothionein promoter is induced by zinc. The SV40 promoter is contained within the plasmid pSV2CAT. The metallothionein promoter is contained within the plasmid pMKCAT. Both the pSV2CAT and pMKCAT were used to transfect K12 cells along with pI10 according to the procedure described in Example XIII. Cell extracts were prepared and the CAT activities were assayed. The conditions tested for pI10 were 35° C for 16 hours in normal DMEM, 16 hours at 39.5° C. in DMEM; 35° C. for 16 hours in glucose-free medium; 35° C. for 16 hours in 7 μM A23187. The plasmid pSV2CAT was tested at 39.5° C. in DMEM, 35° C. for 16 hours in 7 μM A23187. Control samples grown at 35° in DMED show similar activity. The plasmid pMKCAT was tested at 35° C. in DMEM, 35° C. for 16 hours in 7 μM A23187. Induction with $Cd^{2+}$ or $Zn^{2+}$ produced only slightly higher levels than shown.

The results, shown in FIG. 12, demonstrate that the rat GRP regulatory sequence can enhance transcription to levels much higher than the SV40 or metallothionien promoters.

EXAMPLE XV

Enhanced CAT Expression by pT10 in Human Embryo Kidney Fibroblast Cells

To determine if the GRP regulatory sequence is functional in other animal species other than rat and hamster, we transfect human embryo kidney fibroblast cell line 293 with 3 μg of pI10 as described in Example XIII. Cell extracts were prepared from 293 cells treated as follows: 16 hours at 35° C. in normal medium, 16 hours at 35° C. in glucose-free medium, 16 hours at 35° C. in 7 μM A23187. For comparison, the same cells were transformed with 3 μg of pMKCAT, incubated for 16 hours with 100 mM $ZnCl_2$, and 3 μg of pSV2CAT, incubated in 7 μM A23187 DMEM at 35° C.

Figure 13:
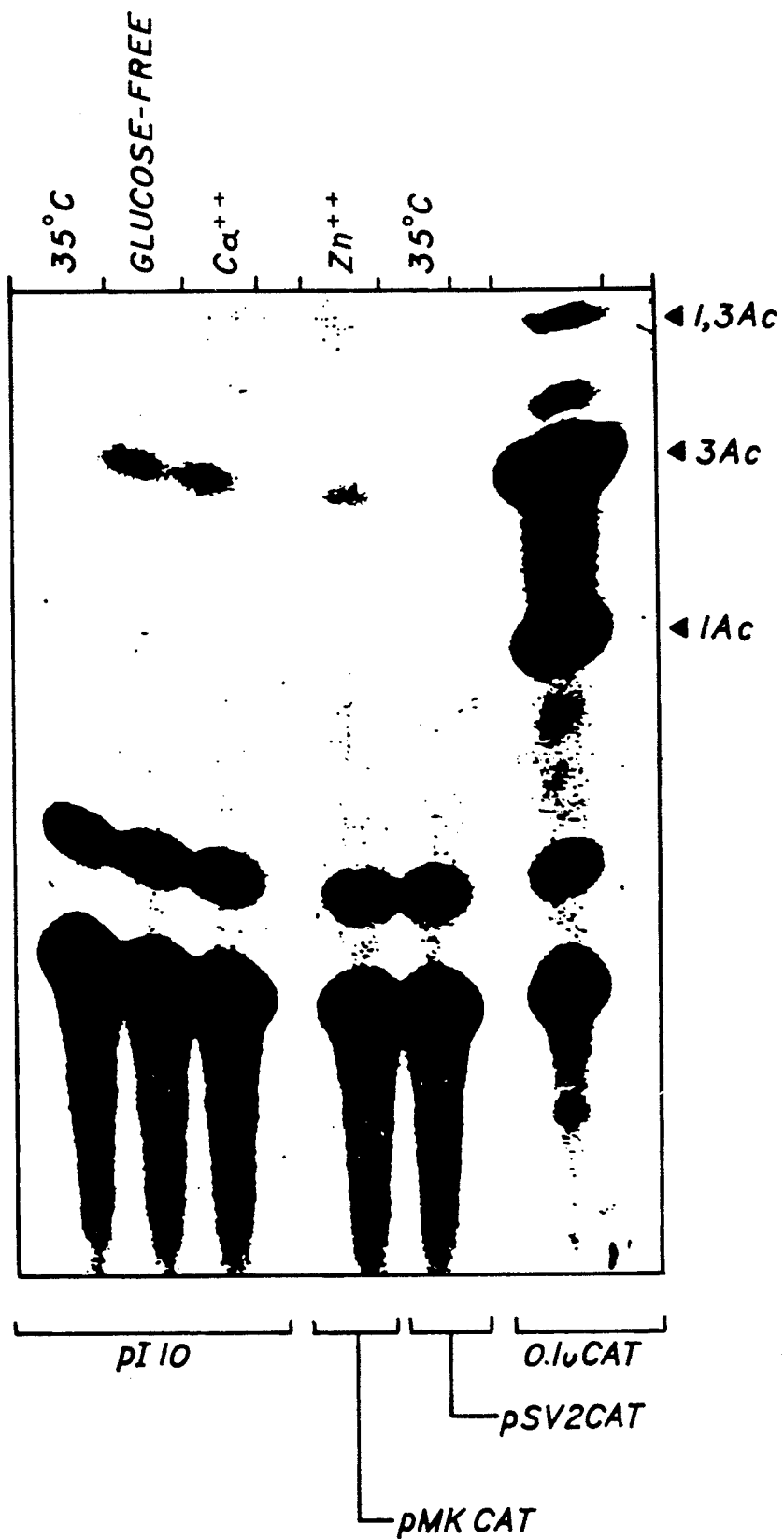
FIG. 13 is an autoradiogram showing CAT activity in human kidney fibroblast cell line 293 transformed by pI10, pMKCAT under various conditions.

The results, as shown in FIG. 13, demonstrate that the GRP regulatory sequence is functional in human cells and is inducible by calcium shock or glucose-starvation. In these assays, the strength of the GRP regulatory sequence was again considerably stronger than that of the SV40 and metallothionein promoters.

The above examples demonstrate that the GRP regulatory sequence is located within the 1.3 kb of the 5' sequence of the RAT 1 DNA and the most important sequences are contained within the SmaI/BsshII fragment of the RAT 1 genomic clone. This region is characterized by its ability to enhance transcription to high levels under conditions of glucose starvation, calcium shock, or high temperature. The ability of the GRP regulatory sequence to enhance transcription in rat, hamster and human cells demonstrates that the DNA sequence within the regulatory sequence responsible for RNA polymerase or recognition and binding is highly conserved. Those skilled in the art will readily recognize that although the RNA polymerase recognition and binding sites are conserved, variations within the GRP78 regulatory sequence DNA sequence will occur from species to species. Accordingly, although we have characterized the GRP78 regulatory sequence by its DNA sequence in FIG. 2, as seen in the following data for human GRP78 regulatory sequences, variations in the nucleotide sequence may occur in non-essential areas of the regulatory sequence and the regulatory sequence will remain functional.

Isolation of Human Gene Encoding Glucose-Regulated Protein

Cell lines and culture conditions

The temperature sensitive (ts) Chinese hamster fibroblast cell line K12 has been described (Roscoe et al., *J. Cell. Physiol.*, 82, 325-332, 1973; Lee, *J. Cell. Physiol.*, 106, 119-332, 1981). It was routinely maintained in DMEM (4.5 mg/ml glucose) supplemented with 10% cadet calf serum. The HeLa D98 AH2 monolayer cells were obtained from R. E. K. Fournier (USC) and were maintained in DMEM with 10% fetal calf serum.

Treatment conditions

HeLa cells grown in 150-mm diameter dishes to 90% confluency 7 μM A23187 for 5 hours (Resendez et al., *Mol. Cell. Biol.*, 5, 212-1219, 1985) or grown in glucose-depleted DMEM for 16 hours (Lin and Lee, *Mol. Cell. Biol.*, 6, 1235-1243, 1984) prior to extraction of cytoplasmic RNA.

EXAMPLE XVI

Isolation of human GRP78 genes

The human fetal liver genomic library (Lawn et al., 1978) was screened using a full-length cDNA plasmid p3C5 which encodes the hamster GRP78 (Lee et al., *J. Cell. Physiol.*, 106, 119-125, 1981). Filters containing about $10^6$ recombinant phage were prehybridized in 50% formamide 5×SSC (1×SSC: 0.15 M NaCl, 15 mM sodium citrate), 5×Denhardt (1×Denhardt: 0.02% each of bovine serum albumin, polyvinylpyrrolidone, and Ficoll), 0.1% NaDodSO4, 50 mM sodium phosphate buffer pH 6.8, 1% glycine, and 100 μg/ml denatured salmon sperm DNA at 42° C. for 1 hour. They were then hybridized in the same buffer with nick-translated p3C5 probe (sp. act. $7 \times 10^7$ cpm/μg; total cpm used $1.5 \times 10^8$) overnight at 42° C. After hybridization, the filters were washed three times at 50° C. for 60 minutes each in 5×Denhardt, 3×SSC, 0.1% NaDodSO$_4$, and 0.1% sodium pyrophosphate; and 2 times at 50° C. for 60 minutes each in 1×SSC, 0.1% NaDodSO$_4$, and 0.1% sodium pyrophosphate. Six recombinant phage hybridized positively with the p3C5 probe.

EXAMPLE XVII

S$_1$ nuclease protection

Figure 14:
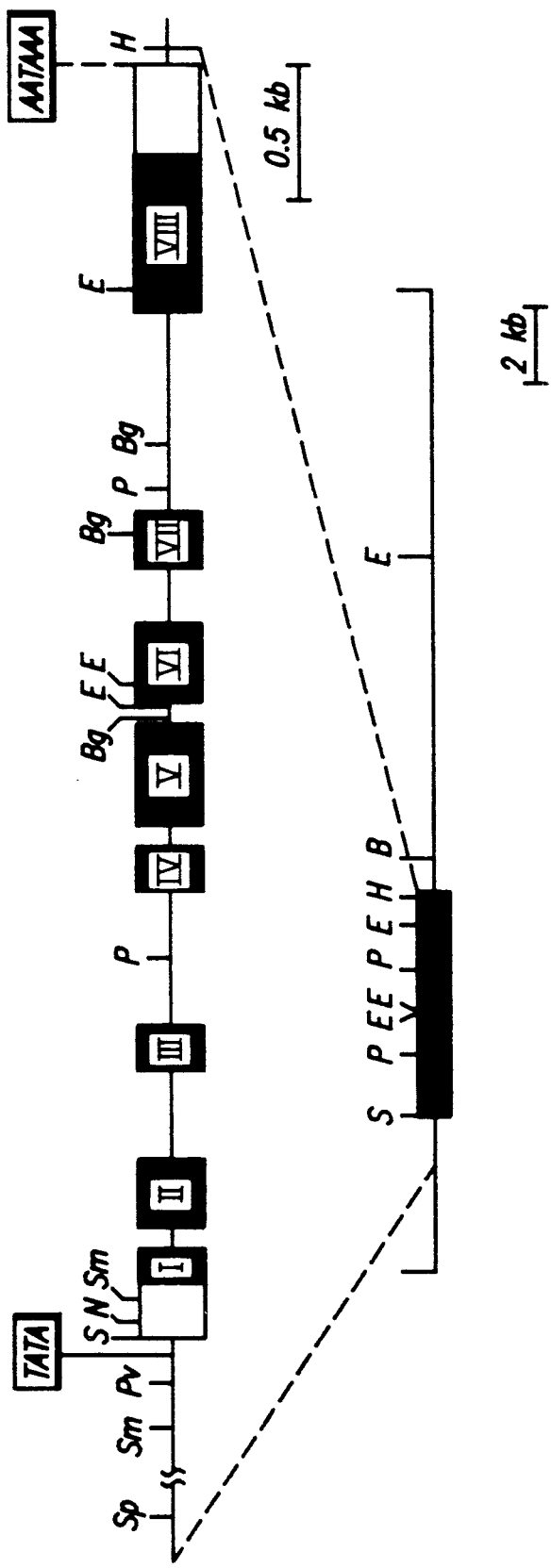
FIG. 14 shows a restriction map and exon structure of the GRP78 gene from clone hu28-1. The lower line shows the restriction map of the 24-kb human genomic DNA within the phage. The upper line shows the expanded exon structure of the GRP78 gene, with the 5' and 3' untranslated regions as open boxes, and the coding region in black, numbered boxes. The TATA box and the poly(A) addition sequence AATAAA are indicated. Restriction enzyme sites marked are: Bam HI(B), Bgl II (Bg), Eco RI (E), Hind III (H), Nru I (N), Pst I (P), Pvu II (Pv), Sal I(S), Sma I (Sm), and Sph I (Sp).

Cytoplasmic RNA was isolated from control and induced HeLa cells as described previously (Resendez et al., Mol. Cell. Biol., 5, 1212-1219, 1985). The DNA probe used for the S$_1$ protection assay was a 497-nucleotide Sma I fragment corresponding to nucleotides −368 to 129 (FIGS. 14 and 17). The DNA Was 5'-end-labeled by T4 polynucleotide kinase (BRL) to a specific activity $6 \times 10^6$ cpm/μg of DNA. About $4 \times 10^5$ cpm of the heat-denatured DNA was hybridized with 30 μg of HeLa RNA in 80% formamide, 0.4 M NaCl, 40 mM PIPES [piperazine-N,N'-bis(2-ethanesulfonic acid)]pH 6.4, and 1 mM EDTA at 58° C. for 16 hours. The DNA-RNA hybrid was then digested with 20 units of S nuclease (PL biochemicals) in 200 μl of reaction mixture containing 0.28 M NaCl, 50 mM sodium acetate pH 4.6, 4.5 mM ZnSC$_4$, and 50 μg/ml of denatured salmon sperm DNA at 37° C. for 30 minutes. Undigested DNA was precipitated with alcohol and electrophoresed on a 6% polyacrylamide sequencing gel.

EXAMPLE XVIII

Primer extension

The primer used was a synthetic oligonucleotide (a 17-mer, with sequence 5'-GGCCGCGACGCTTACCT-3') corresponding to anti-sense nucleotides 24-40 of the rat GRP78 5' UTR. Chang et al., Proc. Natl. Acad. Sci., 84, 660-680 (1987). The primer was labeled by T4 polynucleotide kinase to a specific activity of $1.5 \times 10^8$ cpm/μg DNA. About $10^6$ cpm of the primer was hybridized with 50 μg of HeLa RNA. The hybridization and extension reactions were performed as described Lin et al., Mol. Cell. Biol. 6, 1235-1243 (1986)), with the exception that hybridization was performed at 25° C. for 5 hours in the same hybridization buffer as in S$_1$ nuclease protection experiment.

EXAMPLE XIX

Construction of hybrid genes

To construct plasmids phu78CAT (-1650), phu78CAT (-368), and phu78CAT (-170), DNA fragments Sph I-Nru I (-1650 to 53), Sma I-Sma I (-368 to 129), or Pvu II-Nru I (-170 to 53) containing the human GRP78 promoter and 5' UTR sequences (FIG. 14) were bluntended with T4 DNA polymerase and ligated into the unique Hind III site (blunt-ended with T4 DNA polymerase) of the pSVOCAT vector (Resendez et al., Mol. Cell. Biol., 5, 1212-1219, 1985). Plasmids containing the GRP78 promoter and CAT gene fused in the same transcriptional orientation were identified by restriction mapping.

EXAMPLE XX

Transient transfection conditions and CAT assay

Transfection of DNA into K12 cells and the assays for the chloramphenicol acetyltransferase (CAT) activity have been described (Resendez et al., Mol. Cell. Biol. 5, 1212-1219 (1985)).

EXAMPLE XXI

DNA sequence analysis

The DNA contained within the phage insert was restriction-mapped. Purified DNA fragments were subcloned into M13 vector and sequenced by the dideoxyl chain-termination method (Sanger et al., Proc. Natl. Acad. Sci., USA, 74, 5463-5467, 1977)). Most of the DNA fragments were sequenced on both strands.

EXAMPLE XXII

Isolation of two types of human GRP78 genes

A human genomic library was screened with a full length cDNA probe encoding the hamster GRP78 transcriptional unit. Six positive plaques were isolated; they represented five different lambda clones based on limited restriction mapping. The clones can be further grouped into two restriction patterns, indicating that two different GRP78 genes derived from different regions of the human genome have been isolated. The recombinant phage, hu28-1 and hu3-2B, representing the two types, were selected for detailed restriction mapping and probes derived from the hamster cDNA were used to identify the limits of the coding sequences in the lambda insert (FIGS. 14 and 15). The hu28-1 clone contains a GRP78 gene spanning 5 kb interrupted by intervening sequences, whereas hu3-2B contains a contiguous coding region within 2kb.

EXAMPLE XXIII

The structure of the functional GRP78 gene

Figure 16A:
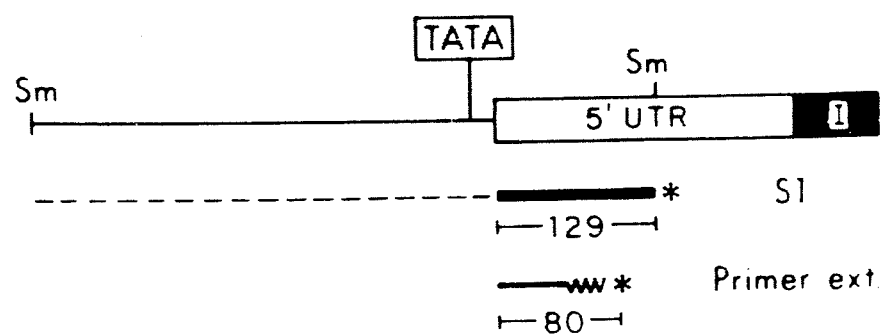
FIG. 16 shows a determination of the transcriptional start site. A. Schematic representation of the probes used for $S_1$ mapping and primer extension. The astericks indicate the kinase-labeled termini. B. $S_1$ mapping of GRP78 transcripts in HeLa cells. RNA samples were from yeast tRNA (lane 1), cells grown continuously in DMEM (lane 2), cells grown in glucose-depleted DMEM for 16 hr (lane 3) and cells grown in DMEM with 7 μM A23187 for 5 hr (lane 4). The lane marked M refers to a size marker from a dideoxy sequencing reaction run in parallel on the same gel. C. Primer extension using a synthetic primer. The RNA samples isolated from HeLa cells grown in the absence (lane 1) or presence of A23187 (lane 2) were used. The resultant DNA fragments were electrophoresed on a 6% polyacrylamide sequencing gel with DNA fragment size markers. The autoradiograms are shown. The sizes (nucleotides) of the major $S_1$ protected band and the primer extension product are indicated.
Figure 16B:
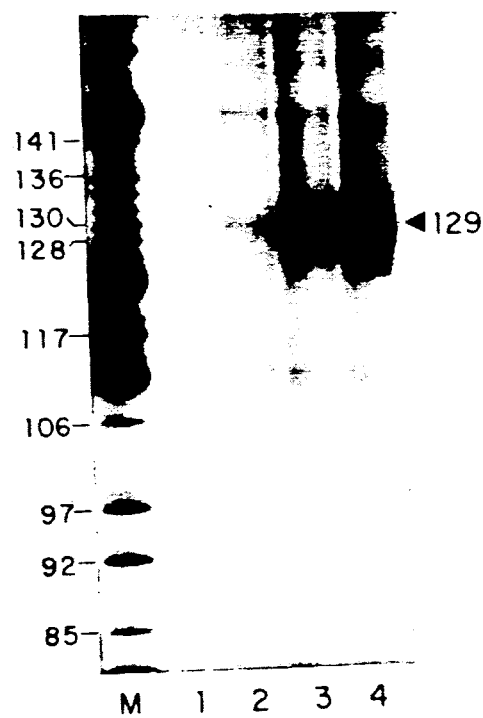
Figure 16C:
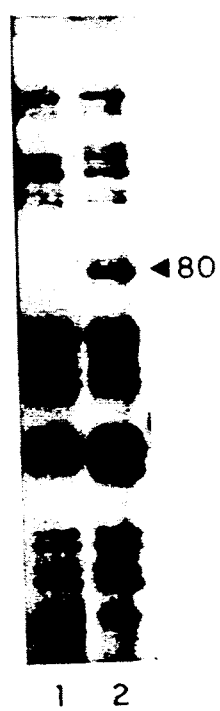

To determine if the GRP78 gene contained within hu28-1 is functional, we searched for canonical promoter and transcriptional initiation and termination elements at 5' and 3' borders of this gene. The transcriptional start site was mapped by both S$_1$ nuclease protection assay and primer extension (FIG. 16). For this purpose, total cytoplasmic RNA was isolated from HeLa cells induced by calcium ionphore A23187 or glucose starvation. As a control, RNA was also extracted from noninduced cells. In the S$_1$ assay, RNA samples were hybridized with a 497-nucleotide Sma I fragment containing the 5' border of the GRP78 gene. As shown in FIG. 3B, the major S1-resistant band has a size of 129 nucleotides. Using the primer extension method, a discrete band of 80 nucleotides corresponding to the site mapped by S$_1$ protection was detected in the induced RNA sample (FIG. 16). The smaller inducible product (63 nucleotides) is probably due to premature stop of the reverse transcriptase. These combined results identified the transcriptional initiation site as 129 nucleotides upstream from the 3 Sma I site. Sequencing the DNA 5' of the cap site revealed a TATA sequence 25 nucleotides upstream. In addition, there are five CCAAT sequences located within 250 nucleotides upstream from the RNA initiation site. Two potential Spl binding sites were localized at −228 and −164. At the 3' end of the gene, a polyadenylation sequence AA- TAAA was also found. All of these features resemble that of a functional gene.

To understand in detail the organization of the GRP78 gene, the complete primary structure of the human GRP78 gene contained in the hu28-1 clone was determined by DNA sequencing. This sequence data, combined with the previously obtained full-length cDNA sequence of the rat and hamster GRP78 (Munro and Pelham, Cell 46, 291–300 (1986); Ting et al., Gene 55, 147–152 (1987)), enabled us to delineate the locations of exon-intron junctions. As shown in FIGS. 14 and 17, clone hu28-1 contains a gene comprising the entire GRP78 coding sequence interrupted by seven intervening sequences. All the exon-intron junctions followed the GT-AG splicing rule (Breathnach et al., Proc. Natl. Acad. Sci., USA 75, 4853–4857 (1978)). Comparing this gene with the rat GRP78 gene, the number and location of the exons are identical. However, the sizes of the intervening sequences are similar but not identical between the rat and human.

EXAMPLE XXIV

GRP78 protein contains highly conserved domains

Figure 18:
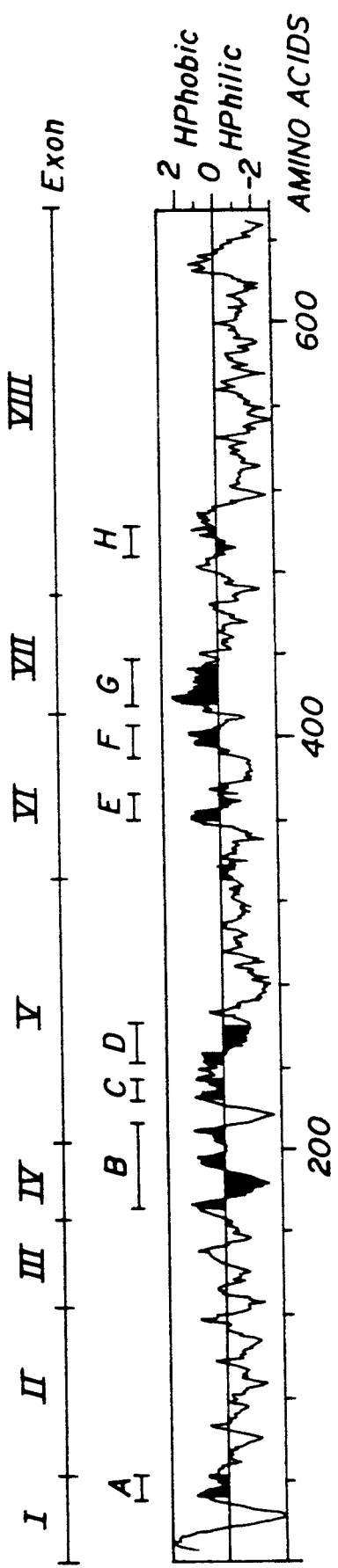
FIG. 18 shows the conservation of amino acid domains in the human GRP78. The hydropathicity profile of the human GRP78 is aligned with the exon boundaries and the amino acid sequence. The shaded regions correspond to domains (A-H) within the human GRP78 amino acid sequence which share over 80% homology with the amino acid sequence reported for the human, Xenopus, Drosophila, yeast, and E. coli heat-shock inducible HSP70 genes. The amino acid sequences of the shared domains are shown in the one-letter code.

The complete amino acid sequence was deduced from the determined nucleotide sequence and was subjected to the hydropathicity analysis (Kyte and Doolittle, J. Mol. Biol. 157, 105–132 (1982)). As shown in FIG. 18, this protein is very hydrophilic, especially toward the carboxyl half of the protein. Only a few small regions were identified to be hydrophobic. Upon comparison of the entire amino acid sequences derived from the human GRP78, rat GRP78, and HSP70 from human, Drosphila, Xenopus, yeast and E. coli dnaK gene, a few regions (A–H) of high sequence homology (over 80%) can be detected (FIG. 18). Similar conservations were observed with the rat hsc73. Strikingly, these domains cover most of the hydrophobic regions of GRP78, including the previously reported 11-amino acid domain (A) near the amino terminus (Chappell et al., Cell 45, 3–13 (1986); and Chang et al., Proc. Natl. Acad. Sci., USA 84, 680–684 (1987)). The other six domains fall into two symmetrical groups of three (B, C, D and E, F, G) around the center of the protein. The most divergent sequences were found at the highly hydrophilic region near the carboxyl third of the protein. Interestingly, the last four amino the endoplasmic reticulum (Munro and Pelham, Cell 48, 899–907 (1987)) are conserved among the human, rat and hamster GRP78 and are lost from the cytoplasmic HSP70.

EXAMPLE XXV

Structure of the processed human GRP78 gene

In contrast to hu28-1, recombinant phage hu3-2B does not contain any introns. The coding region was mapped by hybridization to the hamster DNA and by S1 nuclease digestion, using RNA extracted from HeLa cells (data not shown). These analyses, coupled with sequencing of the DNA flanking the coding region, revealed that this recombinant contains features characteristic of a processed gene (FIG. 15B). First, the coding region is contiguous throughout the gene (Ting, Ph.D. dissertation University of Southern California, Los Angeles, 1988). When compared to the functional gene, we detected a 12-nucleotide deletion close to the amino terminus of the mature protein and a 4-nucleotide insertion within exon VI which results in a shift of the reading frame. In addition, point mutations were found throughout the coding region. At the 3' end of the gene, the consensus sequence for the poly(A) addition site AATAAA was present; shortly downstream from that sequence, there was a stretch of adenosine residues. These results clearly indicate that this gene was derived from a RNA intermediate of the GRP78 gene.

As in the case of other processed genes (Hollis et al., Nature 296, 321–325 (1982); Wilde et al., Nature 297, 83–84 (1982); Karin and Richards, Nature 299, 797–802 (1982)), a short direct repeat sequence, which probably represents the site of insertion of the processed gene, was located flanking the inserted sequence. The repeat is an AT-rich 13-mer with the sequence GAAAAT-TAAACAA. The sequence immediately surrounding the processed gene is strikingly AT rich. The 100-nucleotides upstream from the inserted gene are 66% AT and the 200 nucleotides downstream from the inserted gene are 75% AT. When a 0.9-kb fragment containing the 5'-flanking region of this processed gene was fused to bacterial CAT gene, we could not detect any CAT activity after transient transfection into K12 cells (Ting, Ph.D. dissertation, University of Southern California; Los Angeles, 1988).

EXAMPLE XXVI

Expression and regulation of the human GRP78 promoter

Figure 19A:
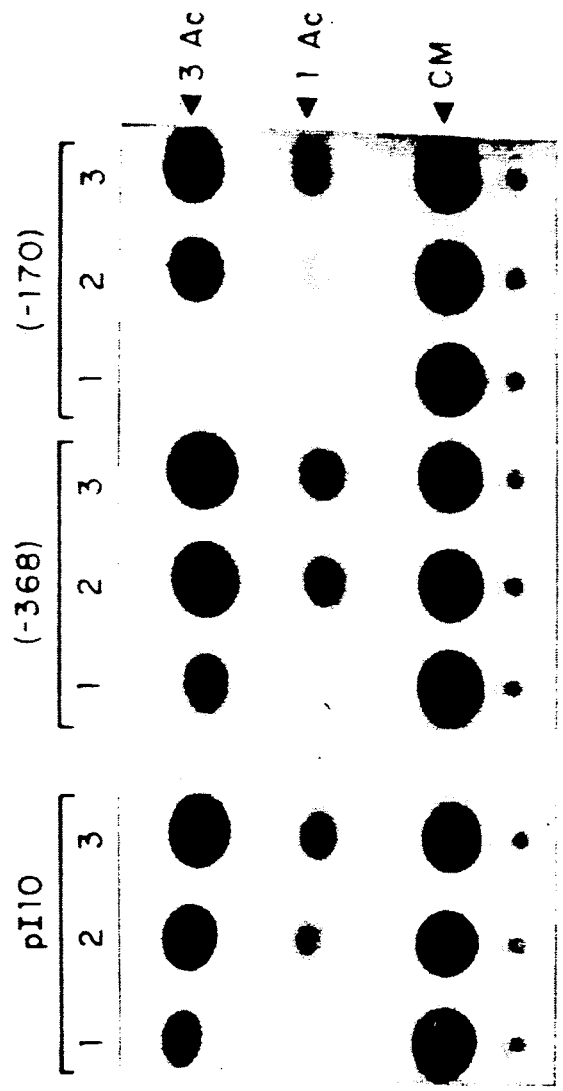
FIG. 19 shows promoter activities of human CRP78-CAT fusion gene constructs. A. K12 cells were transfected with 3 μg of CAT fusion genes containing various lengths (368 and 170 nucleotides upstream from the CAP site) of the human GRP78 promoter. As a comparision, a CAT construct (pI10) which contains 1290 nucleotides of the rat GRP78 promoter (Resendez et al., 1985) is also included. After 30 hours, the cells were either maintained at 35° C. (lane 1), shifted to 40° C. (lane 2), or treated with 7 μM A23187 at 35° C. for 16 hours (lane 3). Protein extracts from the transfectants were assayed for CAT activities. The positions of chloramphenicol (CM) and its acetylated forms (3-Ac and 1-Ac) are indicated. B. Summary of the promoter activities. The promoter features of the GRP78 promoter contained within the CAT fusion gene constructs are schematically presented in the line diagrams. The symbols marked are (black box) TATA, (top half-circle) CCAAT, (bottom half-circle) CCAAT inverted, (black triangle) putative Spl binding site, and (bent arrow) the major RNA initiation site from the GRP78 gene. The results represent the average of three separate experiments and are expressed as a percentage of the activity produced by the −1650 deletion of the human GRP78 promoter in the absence of temperature shift or A23187 treatment.
Figure 19B:
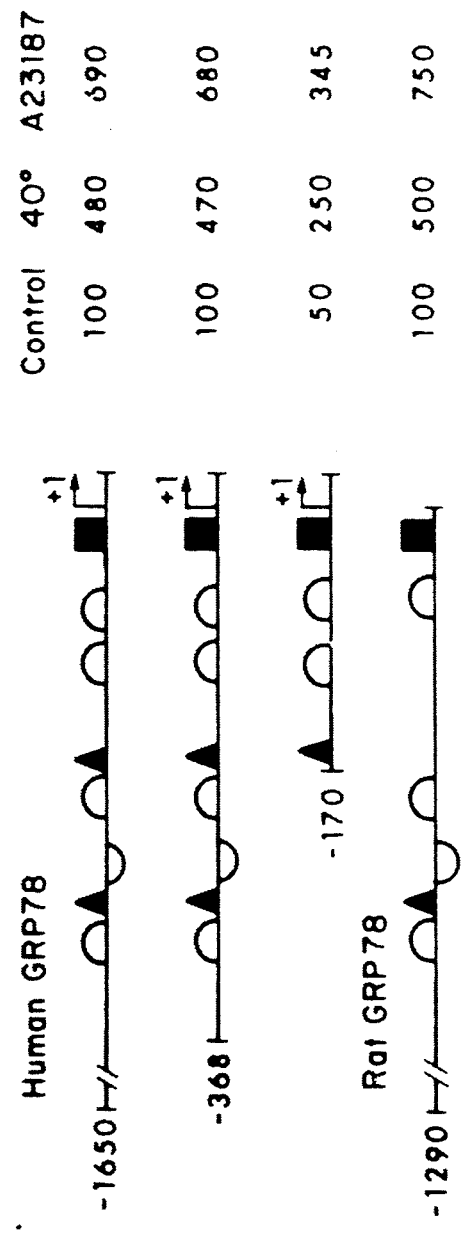

In hamster cells, the GRP78 gene is transcriptionally activated by the calcium ionophore A23187 (Resendez et al., Mol. Cell. Biol. 5, 1212–1219, 1985) and the K12 ts mutation (Lee et al., J. Biol. Chem. 258, 597–603, 1983). By deletion and in vivo competition, the important region for these responses in the rat GRP78 promoter is mapped within 430 nucleotides upstream from TATA box (Lin et al., Mol. Cell. Biol., 6, 1235–1243, 1986; Chang et al., Proc. Natl. Acad. Sci., USA 84, 680–684, 1987). To test if the human GRP78 gene isolated from the hu28-1 clone contains a functional promoter inducible by A23187 and the K12 ts mutation, human GRP78 promoter/CAT fusion genes were constructed and transfected into K12 cells. As a comparison, the CAT fusion gene p110 containing the rat GRP78 promoter (Resendez et al., Mol. Cell. Biol. 5, 1212–1219, 1985) was also tested. After 30 hours, the cells were treated with 7 M A23187 or shifted to the nonpermissive temperature 40° C. Cell extracts were assayed for the CAT activity (FIG. 19A) and the promoter activities of the GRP78/CAT fusion genes under induced or non-induced conditions are summarized (FIG. 19B).

Our results show that the human GRP78 promoter is capable of conferring A23187 and K12 ts mutation induction to the CAT gene. Further, no significant changes were observed at basal or induced activity when the 5'-flanking sequence of the human GRP78 gene was reduced from 1650 nucleotides to 368 nucleotides (our unpublished results and FIG. 19B). When only 170 nucleotides were included, there was a two fold decline in both basal and induced activities. However, all three constructs showed about the same fold of induction at 40° C. and by A23187. On the basis of these results, we conclude that the human GRP78 promoter contains a stressiducible region that responds to A23187 or K12 ts mutation contained within 170 nucleotides upstream from transcriptional initiation site and a distal region at −368 to −170 which enhances the basal level of expression about twofold.

EXAMPLE XXVII

Promoter sequence comparison between human, rat, and chick GRP genes

Comparison of the rat and human GRP78 promoter sequences revealed a strong homology (78%) within 340 nucleotides upstream from the RNA initiation site of the human GRP78 gene (FIG. 20). Several interesting sequences found in the rat GRP78 promoter (Lin et al., *Mol. Cell. Biol.* 6, 1235-1243, 1986) including four CCAAT boxes, and a putative Spl binding site are conserved in the human GRP78 promoter. The proximal 170 nucleotides found to be important for the inductive responses are highly conserved (86%). The distal domain important for high basal level shares about 70% sequence homology. Notably, the rat and human GRP78 promoter sequences start to diverge outside these critical regions. Beyond −340, the sequence homology is less than 20%.

Since the GRP78 and GRP94 genes are activated simultaneously by many stress conditions (Lee, *Trends. Biochem. Sci.* 12, 20–23, 1987), we searched for sequence elements in the GRP78 and GRP94 promoters for consensus sequences which may account for their coordinate regulation. For this purpose, the promoter sequence reported for the chick GRP94 protein (Kleinsek et al., *Nucleic Acids Res.* 14, 10053-10069, 1986; Munro and Pelham, *Cell* 48, 899-907, 1987) is compared with that of the rat and human GRP78 genes. The chick GRP94 promoter sequence is divergent from the rat and human GRP78 promoters except for a region of 22 nucleotides upstream from the TATA sequence (FIG. 20B). This highly conserved region within the three promoters examined lies within the critical region required for A23187 and K12 ts mutation and is devoid of CCAAT and Spl binding sites.

Although the present invention has been described in detail, it should be understood by those of ordinary skill in the art that various modifications can be made without departing from the invention. Accordingly, the invention is limited only by the following claims.

What is claimed is:

1. A recombinant DNA comprising the regulatory sequence of a gene encoding a glucose regulated protein which can effect transcription, or a functional fragment of the regulatory sequence which can effect said transcription, having the nucleic acid sequence for rat shown in FIG. 20.

2. A recombinant DNA comprising the regulatory sequence of a gene encoding a glucose regulated protein which can effect transcription, or a functional fragment of the regulatory sequence which can effect said transcription, wherein the fragment is the 0.292 kb SmaI/StuI fragment.

* * * * *